US011419841B2

(12) United States Patent
Crauste et al.

(10) Patent No.: US 11,419,841 B2
(45) Date of Patent: Aug. 23, 2022

(54) USES OF LIPOPHENOLIC COMPOUNDS

(71) Applicants: Universite De Montpellier, Montpellier (FR); Centre National de la Recherche Scientifique (CNRS), Paris (FR); Ecole Nationale Superieure de Chimie, Montpellier (FR); Institut de Recherche Pour le Developpement (IRD), Marseilles (FR); Universite D'Air-Marseille, Marseilles (FR); Université Côte d'Azur, Nice (FR)

(72) Inventors: Céline Crauste, Montpellier (FR); Joseph Vercauteren, Castelnau le Lez (FR); Francisco Veas, Mauguio (FR); Thierry Durand, Montpellier (FR); Nicolas Blondeau, Nice (FR)

(73) Assignees: Universite De Montpellier; Centre National de la Recherche Scientifique (CNRS); Ecole Nationale Superieure de Chimie; Institut de Recherche Pour le Developpement (IRD); Universite D'Aix-Marseille; Université Côte d'Azur

( * ) Notice: Subject to any disclaimer, the term of this patent is extended or adjusted under 35 U.S.C. 154(b) by 10 days.

(21) Appl. No.: 16/762,739

(22) PCT Filed: Nov. 12, 2018

(86) PCT No.: PCT/EP2018/080915

§ 371 (c)(1),
(2) Date: May 8, 2020

(87) PCT Pub. No.: WO2019/092239

PCT Pub. Date: May 16, 2019

(65) Prior Publication Data

US 2020/0360334 A1 Nov. 19, 2020

(30) Foreign Application Priority Data

Nov. 10, 2017 (EP) .................................... 17306560

(51) Int. Cl.
*A61K 31/235* (2006.01)

(52) U.S. Cl.
CPC .................................. *A61K 31/235* (2013.01)

(58) Field of Classification Search
CPC .... A61K 31/23; A61K 31/231; A61K 31/232; A61K 31/235; C07C 69/22; C07C 69/587
See application file for complete search history.

(56) References Cited

U.S. PATENT DOCUMENTS

2010/0185006 A1* 7/2010 Andrus ................. C07C 67/293
558/270

FOREIGN PATENT DOCUMENTS

| | | | |
|---|---|---|---|
| WO | 9323075 | A1 | 11/1993 |
| WO | 2005069998 | A2 | 8/2005 |
| WO | 2006123178 | A2 | 11/2006 |
| WO | 2015162265 | A1 | 10/2015 |

OTHER PUBLICATIONS

Chen et al. (Acta Tropica, 173, 2017, 76-84) (Year: 2017).*
Berge et al., Pharmaceutical Salts, Journal of Pharmaceutical Sciences, Jan. 1977, pp. 1-19, vol. 66, No. 1.
Blasi et al., Immortalization of murine microglial cells by a v-raf/v-myc carrying retrovirus, Journal of Neuroimmunology, May 1990, pp. 229-237, vol. 27, Elsevier.
Calabriso et al., Red Grape Skin Polyphenols Blunt Matrix Metalloproteinase-2 and 9 Activity and Expression in Cell Models of Vascular Inflammation: Protective Role in Degenerative and Inflammatory Diseases, Molecules, Aug. 2016, 18 pages, 1147, vol. 21, XP055454556.
Chang et al., Development of a Solid Dispersion System for Improving the Oral Bioavailability of Resveratrol in Rats, Eur J Drug Metab Pharmacokinet, published online Apr. 2016, 11 pages.

(Continued)

*Primary Examiner* — Umamaheswari Ramachandran
(74) *Attorney, Agent, or Firm* — Lerner, David, Littenberg, Krumholz & Mentlik, LLP

(57) ABSTRACT

The present invention relates to compound of formula (I):

(I)

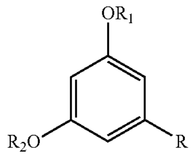

Figure 1:
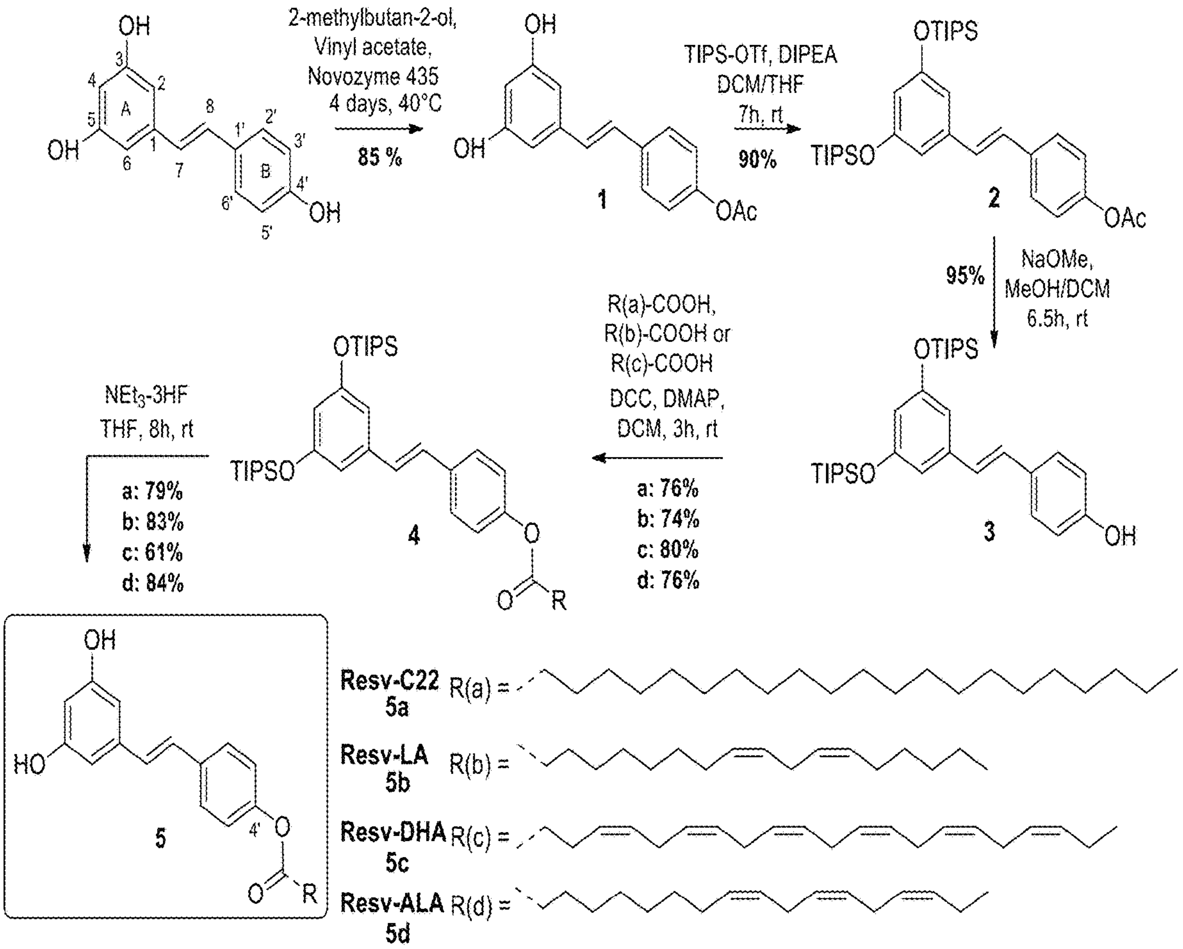

wherein
R is O—$R_3$ or $R_1$ and $R_2$ are identical or different and are each independently H, $(C_1-C_6)$alkyl, —CO—$(C_1-C_{21})$alkyl or —CO—$(C_{11}-C_{21})$alkenyl group, provided that at least one of $R_1$ or $R_2$ is H or $(C_1-C_6)$alkyl,
$R_3$ is a —CO—$(C_{11}-C_{21})$alkyl or —CO—$(C_{11}-C_{21})$alkenyl group,
or its pharmaceutically acceptable salts, racemates, diastereoisomers, enantiomers, or mixtures thereof,
for use in prevention and/or treatment of a disease or disorder linked to an exacerbated vascular, lymphatic or mucosal permeability.

3 Claims, 8 Drawing Sheets

(56) References Cited

OTHER PUBLICATIONS

Cheng et al., Resveratrol inhibits MMP-9 expression by up-regulating PPAR a expression in an oxygen glucose deprivation-exposed neuron model, Neuroscience Letters, Feb. 2009, pp. 105-108, vol. 451, No. 2.
Crauste et al., Synthesis and Evaluation of Polyunsaturated Fatty Acid-Phenol Conjugates as Anti-Carbonyl-Stress Lipophenols, European Journal of Organic Chemistry, Jul. 2014, pp. 4548-4561 (15 pages).
Delaunay et al., Preparative isolation of polyphenolic compounds from Vitis vinifera by centrifugal partition chromatography, Journal of Chromatography A, Jul. 2002, pp. 123-128, vol. 964, Elsevier.
Fulgenzi et al., In Vivo Inhibition of TNFa-Induced Vascular Permeability by Resveratrol, Transplantation Proceedings, May 2001, pp. 2341-2343, vol. 33, XP055454461.
Gao et al., Resveratrol protects primary cortical neuron cultures from transient oxygen-glucose deprivation by inhibiting MMP-9, Molecular Medicine Reports, published online Mar. 2014, pp. 2197-2204, vol. 9, No. 6.
International Search Report for Application No. PCT/EP2018/080915, dated Jan. 28, 2019, pp. 1-4.
Lee et al., Resveratrol inhibits TNF-a-induced proliferation and matrix metalloproteinase expression in human vascular smooth muscle cells, The Journal of Nutrition, Dec. 2005, pp. 2767-2773, vol. 135, No. 12, American Society for Nutrition, XP009503755.
Luplerdlop et al., Dengue-virus-infected dendritic cells trigger vascular leakage through metalloproteinase overproduction, EMBO Reports, Nov. 2006, pp. 1176-1181, vol. 7, No. 11.
Marsac et al., Infection of human monocyte-derived dendritic cells by ANDES Hantavirus enhances proinflammatory state, the secretion of active MMP-9 and indirectly enhances endothelial permeability, Virology Journal, May 2011, pp. 1-9, vol. 8, No. 223.
Misse et al., HIV-1 glycoprotein 120 induces the MMP-9 cytopathogenic factor production that is abolished by inhibition of the p38 mitogen-activated protein kinase signaling pathway, Blood, Aug. 2001, pp. 541-547, vol. 98, No. 3.
Mosmann, Rapid Colorimetric Assay for Cellular Growth and Survival: Application to Proliferation and Cytotoxicity Assays, Journal of Immunological Methods, Dec. 1983, pp. 55-63, vol. 65, Elsevier.
Pany et al., PKC Activation by Resveratrol Derivatives with Unsaturated Aliphatic Chain, PLoS ONE, Dec. 2012, pp. 1-11, vol. 7, No. 12, e52888, XP055454605.
Shamseddin et al., Resveratrol-Linoleate protects from exacerbated endothelial permeability via a drastic inhibition of the MMP-9 activity, Bioscience Reports, Jul. 2018, pp. 1-13, vol. 38. No. 4, BSR20171712, XP055540761.
Walle, Bioavailability of resveratrol, Annals of the New York Academy of Sciences, Jan. 2011, pp. 9-15, vol. 1215.

* cited by examiner (3)-Resv-DHA

Inhibition of TNFa-enhanced permeability of the HUVEC monolayer

USES OF LIPOPHENOLIC COMPOUNDS

CROSS-REFERENCE TO RELATED APPLICATIONS

The present application is a national phase entry under 35 U.S.C. § 371 of International Application No. PCT/EP2018/080915 filed Nov. 12, 2018, which claims priority from EP Application No. 17306560.8 filed Nov. 10, 2017, all of which are incorporated herein by reference.

TECHNICAL DOMAIN

The present invention concerns new uses of lipophenolic compounds, in particular for the prevention and/or treatment of diseases or disorders linked to an exacerbated vascular, lymphatic or mucosal permeability, in particular a chronic or acute disease or disorder, preferably an acute inflammatory disorder.

BACKGROUND OF THE INVENTION

During evolution, the defense mechanisms of organisms (innate immunity) have been strongly selected, therefore highly conserved. In this context, inflammation is a process by which organisms respond to attacks from the 'non-self' (including pathogens, environment, UV radiation, toxic or food, immunity) to maintain the integrity in homeostatic conditions. Inflammation can be due to a variety of reasons or a combination of them including cancer, trauma, infection (HIV, HTLV-1), auto-immunity having serious consequences such as epilepsy and diabetes, viral hemorrhagic fevers (Dengue, Ebola, Hantavirus, Marbug, Lassa), etc.

One of the major consequences of the inflammatory processes is the pathological expression of an increased vascular permeability (IVP), also named exacerbated vascular permeability or enhanced vascular permeability. The permeability according to the invention also encompasses lymphatic or mucosal permeability.

It is known that the activation of target cells such as monocytes (dendritic cells, macrophages) by viruses, including human immunodeficiency virus (HIV), Dengue hemorrhagic virus (DENV) and Hantavirus cardiopulmonary hemorrhage (ANDES-HV) lead to expression of mediators involved in inflammatory process, resulting in the production of proteases, in particular matrix metalloproteases, involved in increased vascular permeability (IVP) (Misse D. et al., 2001; Marsac D. et al., 2011 and Luplertlop N. el al., 2006).

Both MMP-2 and MMP-9, also known as gelatinases, play an important role in several pathological disorders including pulmonary infections, cancer, bronchial asthma, chronic wounds and inflammation, malaria, multiple sclerosis, rheumatoid arthritis, cardiovascular and central nervous system disorders. In particular, MMP-9 is known to destroy the basal lamina, disrupt blood brain barrier (BBB) endothelium and cause an extravasation of phagocytes and parasite-infected erythrocytes, suggesting a main role in Cerebral Malaria CM. In addition, several clinical studies have identified relationships between elevated levels of proinflammatory cytokines (11-b, IL-6, TNF-a), and stroke-induced brain injury. Upon reaching critical levels, these proinflammatory factors contribute to the evolution of tissue injury by two main pathways. They may exert direct cytotoxic effects, like TNF-α (Tumor Necrosis Factor-alpha), threatening neuronal viability in the penumbra or indirect effects promoting leukocyte transmigration across the blood-brain barrier (BBB) that, in consequence, feeds inflammatory cascades, release of oxygen-free radicals and proteolytic enzymes like matrix metalloproteinase-9 (MMP-9) mediating BBB breakdown.

MMP-9 is also over produced in immature dendritic cells infected with dengue virus, and this over activity is associated with elevated level of endothelial permeability (Luplertlop et al. 2006).

So, there is still a need to develop new selective MMP inhibitors for therapeutic applications, in particular MMP-9 inhibitors for preventing and/or treating diseases or disorders linked to an exacerbated (increased) vascular, lymphatic or mucosal permeability.

By 'MMP-9 inhibitors' according to the invention, it means inhibitors of the activity of MMP-9; it can be compounds that exert their effect on the MMP9 activity via the enzymatic activity, expression, post-translational modifications or by other means.

In particular, the Applicant has developed new inhibitors of the activity of MMP-9 for preventing and/or treating diseases or disorders linked to an exacerbated vascular, lymphatic or mucosal permeability, in particular induced and/or aggravated by infectious agents including virus, such as viral hemorrhagic fevers, in particular the ones caused by Dengue or Ebola virus.

Dengue virus (DENV) is classified by the World Health Organization into three categories; dengue with warning signs, dengue without warning signs, and severe dengue. The severe symptoms appearing with an incubation period between 3-8 days, start by sudden fever that lasts between a few days to one week, and the fever is usually associated with headache, myalgia, arthralgia, skin rash, retro ocular pain, nausea and vomiting. The critical phase usually starts after 48 hours when the fever goes down, vascular permeability increases with pleural leakage, ascites, mucosal bleeding, elevated level of hematocrit and shock. In the recovery period, the extravascular fluid is gradually reabsorbed during the treatment followed by secondary skin rash and fatigue that may last for several weeks.

The mechanism of pathogenesis starts when the virus is injected in host after a mosquito bite, the introduced viruses target immune cells monocytes, macrophages and dendritic cells through mannose receptors and dendritic cells-specific ICAM-3-grabbing non-integrin 1 (DC-SIGN), respectively. The infected dendritic cell migrates to the lymph nodes so that it can present the dengue antigen to the T lymphocytes. Once the virions are released, they can infect other immune cells such as monocytes, macrophages and lymphocytes. The virus then can move from lymph nodes to blood through the infected lymphocytes causing further infection and replication that leads to viremia. Antigens presented on major histocompatibility complex (MHC) molecules on the surface of the infected cells activate several types of immune cells, for instance they stimulate the production of IL-2, IL-4, IL-5 and IL-6 by CD4+ and CD8+ cells, IL-1, IL-6 and TNF-α by macrophages and TNF-α and IL-1β by monocytes. All the above-mentioned cytokines and immune mediators serve to increase the vascular permeability, hemorrhage and worsen the prognosis of the disease.

The present invention aims to provide lipophenolic compounds, in particular lipophenolic derivatives of resveratrol, for which the inventors demonstrated an improved inhibition activity of MMP-9 in comparison to resveratrol as such.

Resveratrol, a natural polyphenolic phytoalexin compound that exists in grape stalks, nuts and other plants, has been reported to inhibit the activity of MMP-9 (Cheng et al. 2009, Gao et al. 2014). It also has several biological activities including anti-oxidant, anti-inflammatory and anti-viral activities. Regardless of the above mentioned in vitro biological activities, its use in in vivo treatment is still not considered due to its poor bioavailability (Walle 2011, Chang et al. 2016).

The inventors have now developed lipophenolic derivatives with fatty acid linked to the resorcinol cycle in position 3 (cycle A), or linked to the cycle B in position 4', and tested their ability to inhibit activity of MMP-9 in activated THP-1 cell line. They found that the position of lipids on the resveratrol scaffold structure has an impact on the inhibition activity of MMP9. In particular, 3-Resv-DHA with fatty acid linked to the resorcinol cycle in position 3 did not show any inhibitory activity compare to its region-isomer, 4'-Resv-DHA. All together, these findings show that the resorcinol moiety seems to confer a "structure-activity" relation of the compound. Moreover, saturated fatty-acid are much less flexible than polyunsaturated fatty acids, and the difference in the activity between saturated, DHA (6 double bonds) and LA (2 double bonds) conjugates could have an impact on the affinity of the active site targeted and involved in the inhibition activity of MMP9, the omega-6 linoleic acid incorporated at the 4' position (Resv-LA), giving in the present invention the best activity compared to Resv-DHA and Resv-C22 (Resv-BE).

SUMMARY OF THE INVENTION

A first object of the invention is a compound of formula (I):

(I)

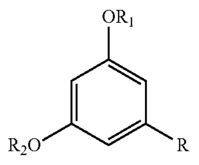

wherein
R is O—$R_3$ or

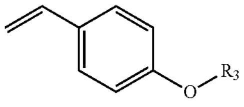

$R_1$ and $R_2$ are identical or different and are each independently H, ($C_1$-$C_6$)alkyl, —CO—($C_1$-$C_{21}$)alkyl or —CO—($C_{11}$-$C_{21}$)alkenyl group, provided that at least one of $R_1$ or $R_2$ is H or ($C_1$-$C_6$)alkyl,
$R_3$ is a —CO—($C_{11}$-$C_{21}$)alkyl or —CO—($C_{11}$-$C_{21}$)alkenyl group,
or its pharmaceutically acceptable salts, racemates, diastereoisomers, enantiomers, or mixtures thereof,
for use in prevention and/or treatment of a disease or disorder linked to an exacerbated (increased) vascular, lymphatic or mucosal permeability, in particular a chronic or acute disease or disorder, preferably an acute inflammatory disorder.

The term 'diseases' and 'disorders' are used interchangeably in the present disclosure.

The term 'treatment' or 'treating' according to the invention means reversing, alleviating, inhibiting the progress of, or preventing the disorder or condition to which such term applies, or one or more symptoms of such disorder or condition.

The inventors demonstrated that the lipophenolic compounds according to the invention are able to protect the endothelial barrier integrity and decrease the exacerbated (increased) vascular, lymphatic or mucosal permeability in infections and other diseases.

The expression 'vascular permeability' according to the invention encompasses endothelial and/or epithelial permeability of the vascular system (i.e cardiovascular system). This expression is used interchangeably with 'vascular leakage' or 'endothelial and/or epithelial exacerbated permeability'.

The present invention also encompasses 'lymphatic permeability' which comprises endothelial and/or epithelial permeability of the vessels of the lymphatic system.

The present invention also encompasses 'mucosal permeability' which comprises endothelial and/or epithelial permeability of the mucous (ex: genital, pulmonar, or digestive system).

So, the generic expression 'permeability' according to the invention encompasses vascular, lymphatic or mucosal permeability.

The expression 'exacerbated or increased vascular permeability' in the present invention means in particular any abnormal (i.e: pathological) increase (or enhancement) of vascular, lymphatic or mucosal permeability associated in particular with inflammation process.

The exacerbated (increased) vascular or lymphatic permeability according to the invention generally results from local (i.e., organs, tissues) or general homeostasis disruption.

The homeostasis is commonly known and may be defined as a tendency of an organism, a cell, an organ or a tissue, to regulate its internal conditions, usually by a system of feedback controls, so as to stabilize health and functioning, regardless of the outside changing conditions.

Such homeostasis disruption can be observed during an exacerbated acute phase immune response (inflammation resulting from a major aggressive cause) or during a chronic inflammatory process. The main actors of such deleterious effects on vascular, lymphatic or mucosal dysfunctions include infectious agents, trauma, allergy, cardiovascular disorders, central nervous system disorders, autoimmune diseases, metabolic diseases and mixtures thereof.

By 'disease or disorder linked to an increased or exacerbated permeability', it means a disease or disorder induced and/or amplified (aggravated) by an increased vascular, lymphatic or mucosal permeability.

In particular, it results from the expression of chronic inflammation or of intense acute phase inflammation observed in particular during chronic or acute conditions, in particular during infectious processes caused by pathogens including viruses.

In a particular embodiment, the disease or disorder is a chronic disease or disorder.

'Chronic' conditions or disorders develop slowly and may worsen over an extended period of time—months to years. They are often caused by unhealthy behaviors that increase the risk of disease—poor nutrition, inadequate physical activity, overuse of alcohol, or smoking. Social, emotional, environmental, and genetic factors also play a role. As people age, they are more likely to develop one or more chronic conditions. The chronic conditions are slower to develop, may progress over time, and may have any number of warning signs or no signs at all. Unlike acute conditions, some chronic health conditions cannot be cured—only controlled.

In another particular and preferred embodiment, the disease or disorder is an acute disease or disorder.

'Acute' conditions or disorders generally develop suddenly and last a short time, often only a few days or weeks. They are often caused by a virus or an infection, but can also be caused by an injury resulting from a trauma as example. They come on rapidly, and are accompanied by distinct symptoms that require urgent or short-term care, and get better once they are treated.

In a particular embodiment, the lipophenolic compounds are for use in prevention and/or treatment of an acute condition, in particular an acute inflammation disorder (acute inflammatory disorder).

An inflammation (inflammation disorder) is an immune reaction that results in localized redness, warmth and swelling. It generally occurs in response to an infection, irritation or injury.

In particular, the disease or disorder linked to an increased or exacerbated permeability is selected from chronic and acute condition, preferably acute condition and in particular infectious diseases, allergies, trauma, cardiovascular disorders, central nervous system disorders, auto-immune diseases, metabolism diseases, or mixtures thereof, which may be induced and/or aggravated by infectious agents.

In a particular embodiment, the lipophenolic compound used according to the invention is administered for a short-term treatment, in particular from 1 to 4 days, and preferably just before and/or during the acute phase response associated with factors inducing the increased vascular, lymphatic or mucosal permeability, including MMP-9. In a particular embodiment, the lipophenolic compound used according to the invention is used in association with at least one additional active compound selected from the group consisting of antibiotic, antiviral, antifungal, antiparasitic, anti-inflammatory active compound and mixtures thereof.

The invention also concerns specific compounds of formula IIb (resveratrol derivatives), pharmaceutical compositions and pharmaceutical kits comprising them.

DETAILED DESCRIPTION OF THE INVENTION

The present invention concerns a compound of formula (I):

(I)

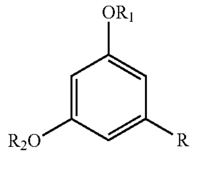

wherein

R is O—$R_3$ or

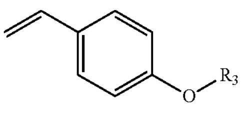

$R_1$ and $R_2$ are identical or different and are each independently H, ($C_1$-$C_6$)alkyl, —CO—($C_1$-$C_{21}$)alkyl or —CO—($C_{11}$-$C_{21}$)alkenyl group, provided that at least one of $R_1$ or $R_2$ is H or ($C_1$-$C_6$)alkyl, $R_3$ is a —CO—($C_{11}$-$C_{21}$)alkyl or —CO—($C_{11}$-$C_{21}$)alkenyl group, or its pharmaceutically acceptable salts, racemates, diastereoisomers, enantiomers, or mixtures thereof, for use in prevention and/or treatment of a disease or disorder linked to an exacerbated (increased) vascular, lymphatic or mucosal permeability.

The compounds used in the invention are lipophenolic compounds and thus phenolic derivatives. They comprise a phenyl group which may carry one or several phenol functions, preferably two (resveratrol derivatives), each being possibly alkylated or acylated. Each compound according to the invention comprises at least one lipidic chain (also named fatty acid chain) which corresponds to the $R_3$ radical. The compounds used in the invention may also be called fatty acid-phenolic conjugates or derivatives as they comprise a phenolic core on which is linked at least one fatty acid chain. In a preferred embodiment, for the resveratrol derivatives (formula IIb disclosed hereunder), the fatty acid chain is on position 4'. The inventors demonstrated that such resveratrol compounds with fatty acid chain on position 4' have a MMP-9 inhibitory activity, whereas resveratrol derivatives with fatty acid chain in position 3 do not have any detectable MMP-9 inhibitory activity.

The hydrophilic/lipophilic balance is adjusted by a covalent grafting of a lipid molecule (a fatty acid) on the phenol structure, preferably the resveratrol, and designs new lipophenolic derivatives. These resveratrol-linked fatty acids or fatty-acid resveratrol derivatives include in particular saturated fatty acid (docosanoic acid or behenic acid, C22:0, Resv-C22 also named Resv-BE), omega-6 polyunsaturated fatty acid using linoleic acid (C18:2 n-6, Resv-LA), and omega-3 polyunsaturated fatty acid such as docosahexaenoic acid (C22:6 n-3, Resv-DHA) and linolenic acid (C18:3 n-3, Resv-ALA).

The term "an alkyl group" according to the invention means a linear or branched, saturated, hydrocarbon-based aliphatic group comprising, unless otherwise mentioned, from 1 to 12 carbon atoms. By way of examples, mention may be made of methyl, ethyl, n-propyl, isopropyl, butyl, isobutyl, tert-butyl or pentyl groups.

The term "alkenyl" according to the invention includes partially unsaturated, nonaromatic, hydrocarbon groups.

The term "pharmaceutically acceptable salts" refers to salts which retain the biological effectiveness and properties of the compounds of the invention and which are not biologically or otherwise undesirable. Pharmaceutically acceptable acid addition salts may be prepared from inorganic and organic acids, while pharmaceutically acceptable base addition salts can be prepared from inorganic and organic bases. For a review of pharmaceutically acceptable salts see Berge, et al. ((1977) "*Pharmacologically acceptable salts*" J. Pharm. Sd, vol. 66, 1). For example, the salts include those derived from inorganic acids such as hydrochloric, hydrobromic, sulfuric, sulfamic, phosphoric, nitric, and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, fumaric, methanesulfonic, and toluenesulfonic acid and the like.

In a particular embodiment, the radical R in the compound of formula (I)

(I)

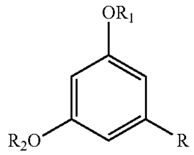

is O—$R_3$.

Such lipophenolic compounds, also named 'fatty-acid phloroglucinol derivatives' have formula (Ia), and preferably formula (Ib) as disclosed hereunder:

(IIa)

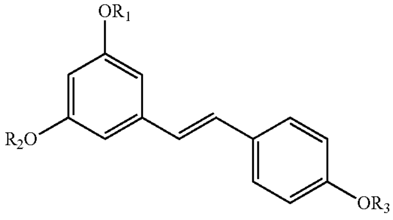

(IIb)

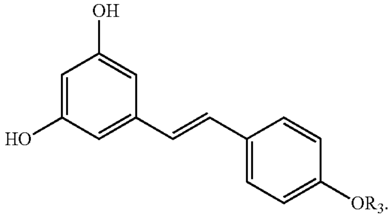

The radicals $R_1$, $R_2$ and $R_3$ are defined above and in the following description.

In a particular and preferred embodiment, the radical R in the compound of formula (I)

(I)

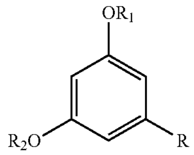

is

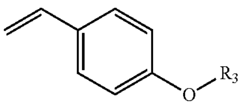

Such lipophenolic compounds, also named 'fatty-acid resveratrol derivatives' have formula (IIa), and preferably formula (IIb) as disclosed hereunder:

(IIa)

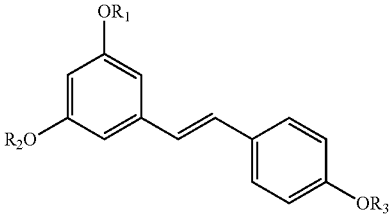

(IIb)

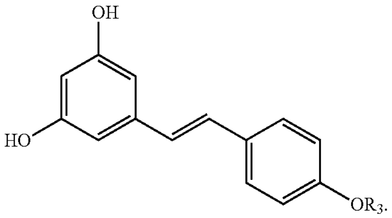

The radicals $R_1$, $R_2$ and $R_3$ are defined above and in the following description.

In a particular embodiment, the radicals $R_1$, $R_2$ and $R_3$ in the compound of formula (I)

(I)

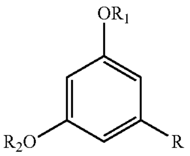

wherein R is O—$R_3$ or

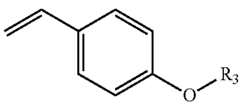

are respectively:

$R_1$ is $R_3$ and $R_2$ is H or ($C_1$-$C_6$)alkyl, or $R_2$ is $R_3$ and $R_1$ is H or ($C_1$-$C_6$), alkyl.

In a particular embodiment, $R_1$ and $R_2$ are both H.

In a particular and preferred embodiment, the radical R in the compound of formula (I)

(I)

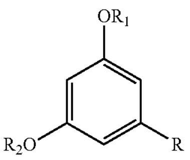

is

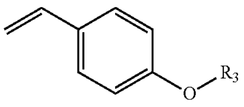

and $R_1$ and $R_2$ are both H, corresponding to the compound of formula (IIb)

(IIb)

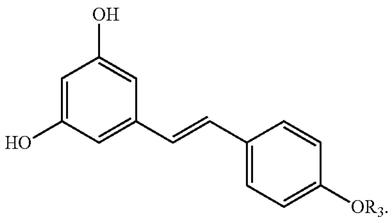

In a particular embodiment, $R_3$ is a linear —CO—($C_{11}$-$C_{21}$) alkyl or —CO—($C_{11}$-$C_{21}$) alkenyl group.

In particular, $R_3$ is a linear —CO—($C_{15}$-$C_{21}$) alkyl chain, with said alkyl chain preferably containing an uneven number of carbon atoms, or a linear —CO—($C_{15}$-$C_{21}$)alkenyl chain, with said alkenyl chain preferably containing an uneven number of carbon atoms and advantageously cis double bond(s).

In a preferred embodiment, $R_3$ is selected from the group consisting of:

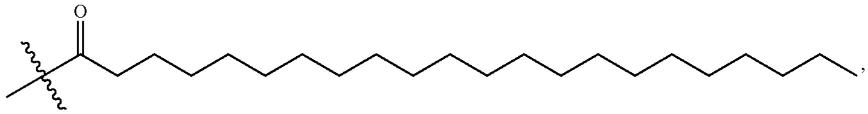 [SMILES: *C(=O)CCCCCCCCCCCCCCCCCCCCC],

- also named docosanoic ($C_{22}$) or behenic acid (BE) derivative,

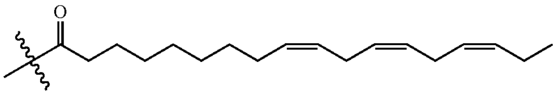, also named linolenic acid (ALA) derivative

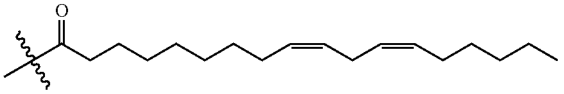, also named linoleic acid (LA) derivative or

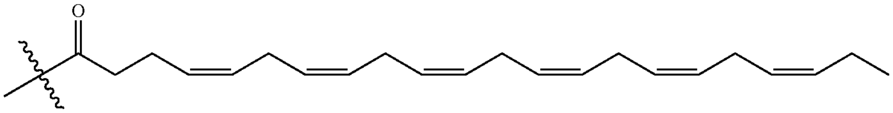, also named docosahexanoic acid (DHA) derivative preferably

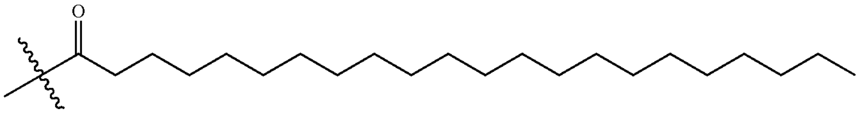,

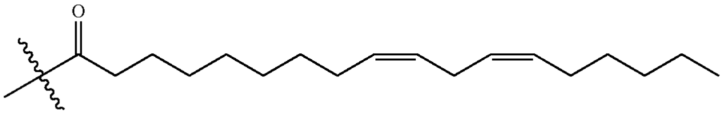, or

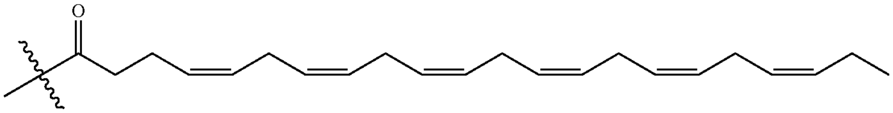 [SMILES: *C(=O)CC/C=C\C/C=C\C/C=C\C/C=C\C/C=C\C/C=C\CC]

and more preferably
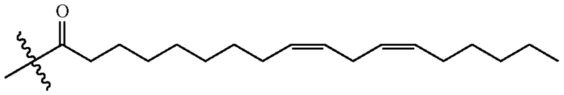
.
In a particular and preferred embodiment, lipophenolic compound used in the invention is a compound of formula (IIb), also named fatty-acid resveratrol derivative in position 4'
(IIb)
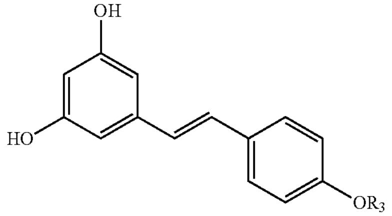
with $R_3$ selected from the group consisting of:
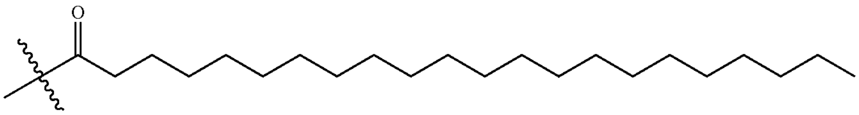
,
also named Resv-$C_{22}$ or Resv-BE
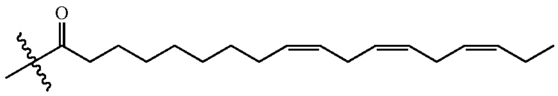
,
also named Resv-ALA
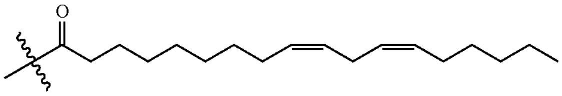
,
also named Resv-LA or
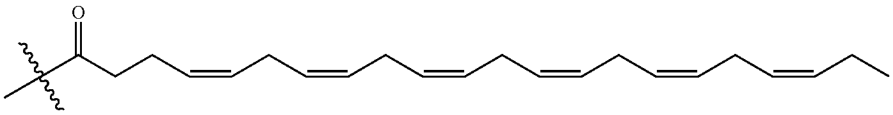
also named Resv-DHA
preferably
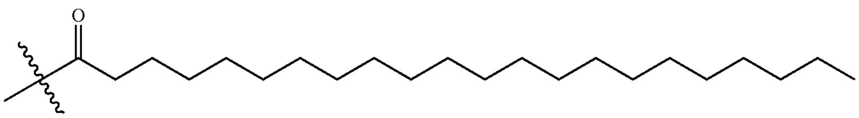
,
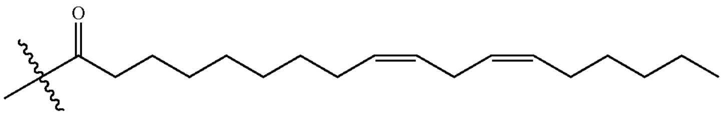
, or
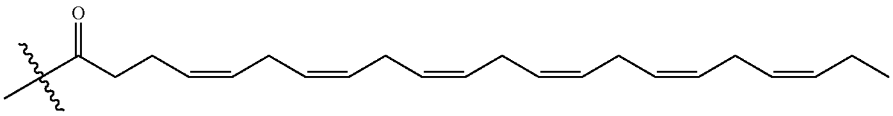

and more preferably

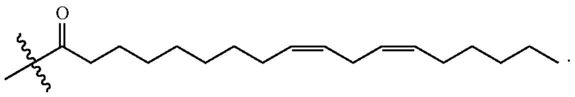 [SMILES: *C(=O)CCCCCCC/C=C\C/C=C\CCCCC]

In a more preferred embodiment, the lipophenolic compound used in the invention is a compound of formula (IIb), (IIb)

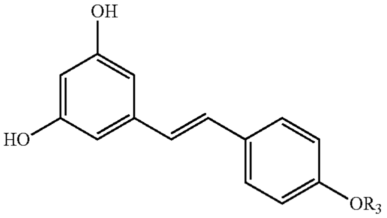

with $R_3$ being

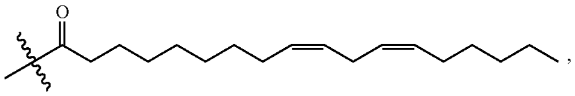 [SMILES: *C(=O)CCCCCCC/C=C\C/C=C\CCCCC]

also named Resv-LA.

The lipophenolic compounds as disclosed above are used according to the invention to protect the endothelial barrier integrity and decrease the exacerbated (increased) vascular, lymphatic or mucosal permeability, which generally results from local (i.e., organs, tissues) or general homeostasis disruption.

As disclosed above, the main actors of such deleterious effects on vascular, lymphatic or mucosal dysfunctions include infectious agents, trauma, allergy, cardiovascular disorders, central nervous system disorders, autoimmune diseases, metabolic diseases and mixtures thereof.

So, the disease or disorder linked to an exacerbated vascular, lymphatic or mucosal permeability according to the invention is in particular selected from chronic and acute condition, preferably acute condition, and in particular infectious diseases, trauma, allergy, cardiovascular disorders, central nervous system disorders, autoimmune diseases, metabolic diseases and mixtures thereof, which may be induced and/or aggravated by infectious agents.

In particular, the disease or disorder linked to exacerbated vascular, lymphatic or mucosal permeability is induced and/or aggravated by infectious agents, in particular virus, and is selected preferably from central nervous system disorders, auto-immune diseases and viral infections, more preferably from viral hemorrhagic fevers and in particular the ones caused by Dengue or Ebola virus.

In a particular embodiment, the lipophenolic compounds as disclosed above are used according to the invention to decrease the exacerbated (increased) vascular, lymphatic or mucosal permeability induced and/or aggravated by infectious agents causing infectious diseases.

In another embodiment, the lipophenolic compounds as disclosed above are used according to the invention to decrease the exacerbated (increased) vascular, lymphatic or mucosal permeability induced and/or aggravated by a trauma.

The term 'trauma' according to the invention refers to injury or damage to a biological organism caused by physical harm from an external source. Mentioned may be made in particular of cardiovascular event or 'stroke' or injuries caused during combat sports (e.g boxing) or contact sports (e.g rugby).

In another embodiment, the lipophenolic compounds as disclosed above are used according to the invention to decrease the exacerbated (increased) vascular, lymphatic or mucosal permeability induced and/or aggravated by an allergy.

In another embodiment, the lipophenolic compounds as disclosed above are used according to the invention to decrease the exacerbated (increased) vascular, lymphatic or mucosal permeability induced and/or aggravated by a cardiovascular disorder. Mention may be made in particular of heart failure, cardiovascular event or stroke.

In another embodiment, the lipophenolic compounds as disclosed above are used according to the invention to decrease the exacerbated (increased) vascular, lymphatic or mucosal permeability induced and/or aggravated by central nervous system disorder. Mention may be made in particular of encephalitis, epilepsy.

In another embodiment, the lipophenolic compounds as disclosed above are used according to the invention to decrease the exacerbated (increased) vascular, lymphatic or mucosal permeability induced and/or aggravated by autoimmune diseases. Mention may be made in particular of multiple sclerosis.

In another embodiment, the lipophenolic compounds as disclosed above are used according to the invention to decrease the exacerbated (increased) vascular, lymphatic or mucosal permeability induced and/or aggravated by metabolic diseases. Mention may be made in particular of diabetes.

In a particular preferred embodiment, the lipophenolic compounds are used to decrease the exacerbated (increased) vascular, lymphatic or mucosal permeability induced and/or aggravated by infectious agents (e.g virus, bacteria, parasite or fungus).

In a first preferred embodiment, the lipophenolic compounds are used to decrease the exacerbated (increased) vascular, lymphatic or mucosal permeability induced and/or aggravated by an infectious agent causing an inflammation of the central nervous system also named 'central nervous system disorder'.

The term 'inflammation of the central nervous system' or 'central nervous system disorder' according to the invention, refers the inflammation of the brain (encephalitis) and the spinal cord as well as the tissues that protect the brain called meninges. Encephalitis with meningitis is known as meningoencephalitis. General symptoms include headache, fever, confusion, dizziness drowsiness, fatigue, reaching seizures or convulsions, tremors, hallucinations, stroke, and/or memory dysfunctions.

Inflammation of the nervous system, and in particular encephalitis can be caused by viral infection (e.g.: rabies virus, HSV infection, poliovirus, and measles virus may cause acute viral encephalitis such as Japanese encephalitis virus, Nipah virus, Zika virus, Hendra virus, West Nile virus, Herpes simplex virus etc) or bacterial infection (e.g.: bacterial meningitis); parasitic infection (e.g.: toxoplasma, malaria, etc) as well as fungi (e.g.: cryptococcidiosis, candidiasis, aspergillosis). In another hand, as disclosed above, encephalitis may be caused by inflammatory cascades: proinflammatory factors (cytokines), upon reaching critical levels, contribute to the evolution of tissue injury either by exerting direct cytotoxic effects, like TNF-α threatening neuronal viability in the penumbra or indirect effects promoting leukocyte transmigration across the blood-brain barrier (BBB) that, in consequence, feeds inflammatory cascades, release of oxygen-free radicals and proteolytic enzymes like matrix metalloproteinase-9 (MMP-9) mediating BBB breakdown and nervous system disorders, in particular encephalitis.

In a second preferred embodiment, the lipophenolic compounds are used to decrease the exacerbated (increased) vascular, lymphatic or mucosal permeability induced and/or aggravated by a virus causing a viral hemorrhagic fever.

The most evident examples of this exacerbated vascular leakage are induced by viruses causing hemorrhagic fevers (VHFs), which is a diverse group of animal and human illnesses (e.g: RNA viruses: the families Arenaviridae, Filoviridae, Bunyaviridae, Flaviviridae, and Rhabdoviridae). All types of VHF are characterized by fever and bleeding disorders and all can progress to high fever, shock and death in most of the cases. Some of the VHF agents cause relatively mild illnesses, such as the Scandinavian nephropathia epidemica (a Hantavirus), while others, such as Ebola, Lassa, Crimean-Congo hemorrhagic fever, CCHF, Marburg viruses, and the South American hemorrhagic fevers caused by arenaviruses most of the times cause severe, life-threatening disease, only observed in a small percentage of patients with Dengue, Rift Valley or Lassa virus infection.

Five families of RNA viruses have been recognized as being able to cause hemorrhagic fevers:

- Arenaviridae: include the viruses responsible for Lassa fever (Lassa virus), Lujo virus, Argentine (Junin virus), Bolivian (Machupo virus), Brazilian (Sabiá virus), Chapare hemorrhagic fever (Chapare virus) and Venezuelan (Guanarito virus) hemorrhagic fevers;
- Bunyaviridae: include the members of the Hantavirus genus that cause hemorrhagic fever with renal syndrome (HFRS), the Crimean-Congo hemorrhagic fever (CCHF) virus from the Nairovirus genus, Garissa virus and Ilesha virus from the Orthobunyavirus and the Rift Valley fever (RVF) virus from the Phlebovirus genus;
- Filoviridae: include Ebola virus and Marburg virus;
- Flaviviridae: include dengue, yellow fever, and two viruses in the tick-borne encephalitis group that cause VHF: Omsk hemorrhagic fever virus and Kyasanur Forest disease virus; and
- Rhabdoviridae.

In particular, the prevention and/or treatment of the disease or disorder according to the invention resulted from the reduction, by using lipophenolic compounds of formula (I) according to the invention, of the active MMP9-induced endothelial or epithelial hyper-permeability.

In particular embodiments, the lipophenolic compounds of formula (I) according to the inventions, ie fatty-acid phloroglucinol derivatives, are used for prevention and/or treatment of diseases as defined above and listed in the following Table 1:

| Fatty-acid phloroglucinol derivatives according to formula (I) | Central nervous system disorders (ex: encephalitis) | Infectious diseases, in particular caused by a virus | Viral hemorrhagic fevers (ex: Dengue, Ebola) | Allergies | Trauma (ex: stroke, combat sports) | Auto-immune diseases (ex: multiple sclerosis) | Cardiovascular diseases (ex: heart failure, stroke) | Metabolic diseases (ex: diabete) |
|---|---|---|---|---|---|---|---|---|
| 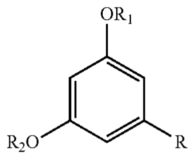 (I) wherein R is O—$R_3$ $R_1$ and $R_2$ are identical or different and are each independently H, ($C_1$-$C_6$)alkyl, —CO—($C_1$-$C_{21}$)alkyl or —CO—($C_{11}$-$C_{21}$)alkenyl group, provided that at | x | xx | xxx | xx | xx | x | x | x |

-continued

| Fatty-acid phloroglucinol derivatives according to formula (I) | Central nervous system disorders (ex: encephalitis) | Infectious diseases, in particular caused by a virus | Viral hemorrhagic fevers (ex: Dengue, Ebola) | Allergies | Trauma (ex: stroke, combat sports) | Auto-immune diseases (ex: multiple sclerosis) | Cardiovascular diseases (ex: heart failure, stroke) | Metabolic diseases (ex: diabete) |
|---|---|---|---|---|---|---|---|---|
| least one of $R_1$ or $R_2$ is H or $(C_1\text{-}C_6)$alkyl, $R_3$ is a —CO—$(C_{11}\text{-}C_{21})$alkyl or —CO—$(C_{11}\text{-}C_{21})$alkenyl group | | | | | | | | |
| Wherein R1 and R2 = H | xxx | xx | xxx | xx | xxx | xxx | xx | xx |
| Wherein R1 and R2 = H and R3 is a linear —CO—$(C_{11}\text{-}C_{21})$alkyl or —CO—$(C_{11}\text{-}C_{21})$alkenyl group, preferably —CO—$(C_{15}\text{-}C_{21})$alkyl or —CO—$(C_{15}\text{-}C_{21})$alkenyl group. | xxx | xx | xxx | xx | xxx | xxx | xx | xx |
| Wherein R1 and R2 = H and R3 is —CO—$(C_{22})$alkyl group | xxx | xx | xxx | xx | xxx | xxx | xx | xx |
| Wherein R1 and R2 = H and R3 is —CO—$(C_{18})$alkenyl group with 2 double bonds | xxx | xx | xxx | xx | xxx | xxx | xx | xx |
| Wherein R1 and R2 = H and R3 is —CO—$(C_{22})$alkenyl group with 6 double bonds | xxx | xx | xxx | xx | xxx | xxx | xx | xx |

All the combinations of fatty-acid phloroglucinol derivatives with diseases disclosed above in the table 1 are encompassed by the present invention. The combinations 'xx' are preferred and the combinations 'xxx' are more preferred.

In particular and preferred embodiments, the lipophenolic compounds of formula (IIa) and (IIb) according to the inventions, ie fatty-acid resveratrol derivatives, are used for the prevention and/or treatment of diseases as defined above and listed in the following Table 2:

| Fatty-acid resveratrol derivatives according to formula (II) | Central nervous system disorders (ex: encephalitis) | Infectious diseases, in particular caused by a virus | Viral hemorrhagic fevers (ex: Dengue, Ebola) | Allergies | Trauma (ex: stroke, combat sports) | Auto-immune diseases (ex: multiple sclerosis) | Cardiovascular diseases (ex: heart failure, stroke) | Metabolic diseases (ex: diabete) |
|---|---|---|---|---|---|---|---|---|
| 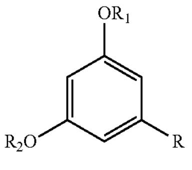<br>(I)<br>wherein<br>R is<br>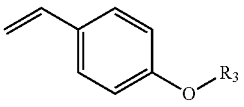 | xxx | xx | xxx | xx | xxx | xxx | xx | xx |

-continued

| Fatty-acid resveratrol derivatives according to formula (II) | Central nervous system disorders (ex: encephalitis) | Infectious diseases, in particular caused by a virus | Viral hemorrhagic fevers (ex: Dengue, Ebola) | Allergies | Trauma (ex: stroke, combat sports) | Auto-immune diseases (ex: multiple sclerosis) | Cardiovascular diseases (ex: heart failure, stroke) | Metabolic diseases (ex: diabete) |
|---|---|---|---|---|---|---|---|---|
| $R_1$ and $R_2$ are identical or different and are each independently H, $(C_1\text{-}C_6)$alkyl, —CO—$(C_1\text{-}C_{21})$alkyl or —CO—$(C_{11}\text{-}C_{21})$alkenyl group, provided that at least one of $R_1$ or $R_2$ is H or $(C_1\text{-}C_6)$alkyl, $R_3$ is a —CO—$(C_{11}\text{-}C_{21})$alkyl or —CO—$(C_{11}\text{-}C_{21})$alkenyl group | | | | | | | | |
| Wherein R1 and R2 = H | xxx | xx | xxx | xx | xxx | xxx | xx | xx |
| Wherein R1 and R2 = H and R3 is a linear —CO—$(C_{11}\text{-}C_{21})$alkyl or —CO—$(C_{11}\text{-}C_{21})$alkenyl group, preferably —CO—$(C_{15}\text{-}C_{21})$alkyl or —CO—$(C_{15}\text{-}C_{21})$alkenyl group. | xxx | xx | xxx | xx | xxx | xxx | xx | xx |
| Wherein R1 and R2 = H and R3 is —CO—$(C_{22})$alkyl group (Resv-C22 or Resv-BE) | xxx | xx | xxx | xx | xxx | xxx | xx | xx |
| Wherein R1 and R2 = H and R3 is —CO—$(C_{18})$alkenyl group with 2 double bonds (Resv-LA) | xxx | xx | xxx | xx | xxx | xxx | xx | xx |
| Wherein R1 and R2 = H and R3 is —CO—$(C_{22})$alkenyl group with 6 double bonds (Resv-DHA) | xxx | xx | xxx | xx | xxx | xxx | xx | xx |

All the combinations of fatty-acid resveratrol derivatives with diseases disclosed in the table 1 are encompassed by the present invention. The combinations 'xx' are preferred and the combinations 'xxx' are more preferred.

In a particular and preferred embodiment, the lipophenolic compound is of formula (IIb), (IIb)

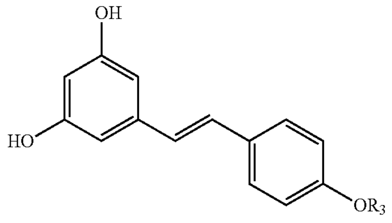

with $R_3$ selected from the group consisting preferably of:

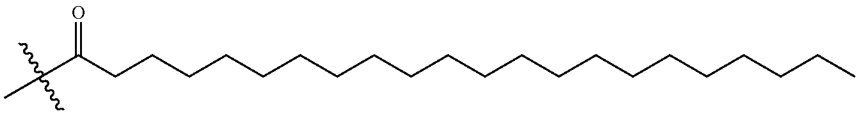

,

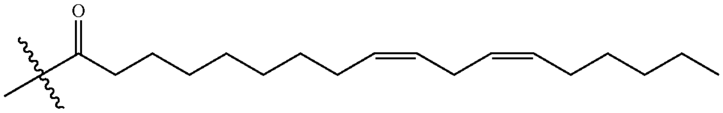

or

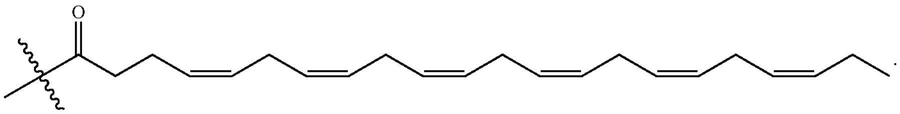 [SMILES: *C(=O)CC/C=C\C/C=C\C/C=C\C/C=C\C/C=C\C/C=C\CC]

.

and more preferably

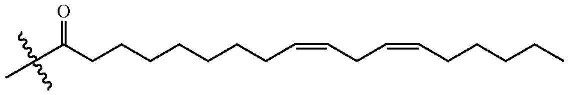 [SMILES: *C(=O)CCCCCCC/C=C\C/C=C\CCCCC]

and the disease is selected from viral infections, and preferably viral hemorrhagic fevers, in particular the ones caused by Dengue or Ebola virus.

In a particular and preferred embodiment, the lipophenolic compound is of formula (IIb), (IIb)

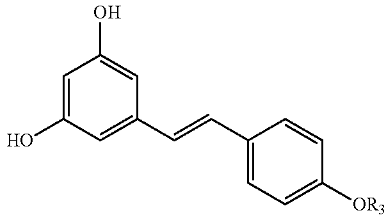

with $R_3$ selected from the group consisting preferably of:

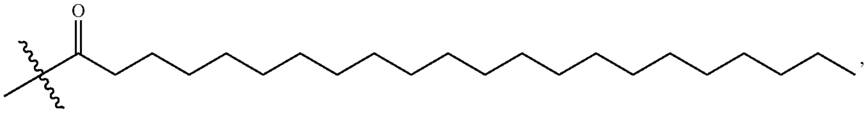

,

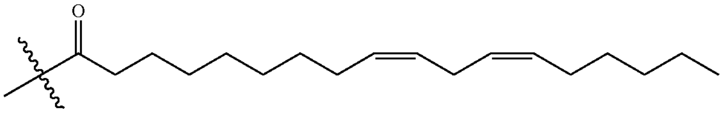

or

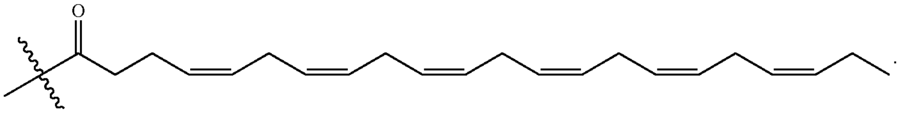

.

and more preferably

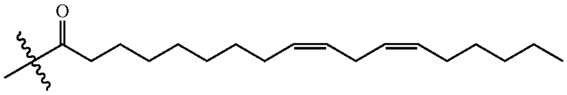 [SMILES: *C(=O)CCCCCCC/C=C\C/C=C\CCCCC]

and the disease is selected from auto-immune diseases, and preferably multiple sclerosis.

In a particular and preferred embodiment, the lipophenolic compound is of formula (IIb), (IIb)

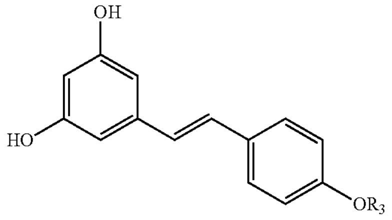

with $R_3$ selected from the group consisting preferably of:

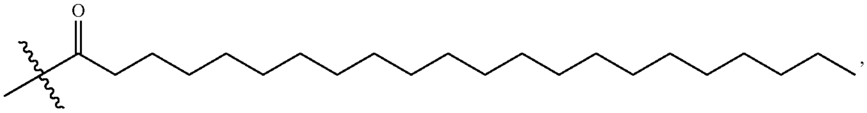

,

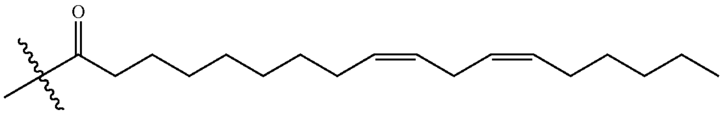

or

-continued
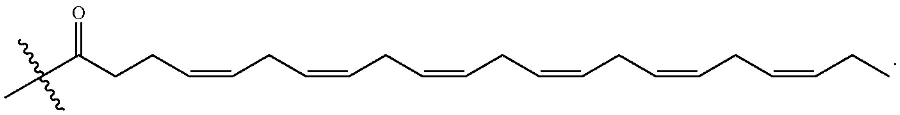
and more preferably
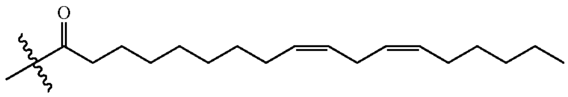 [SMILES: *C(=O)CCCCCCC/C=C\C/C=C\CCCCC]
and the disorder is selected from trauma, in particular cardiovascular event or stroke or injury during combat sports or contact sports.
In a particular and preferred embodiment, the lipophenolic compound is of formula (IIb),
(IIb)
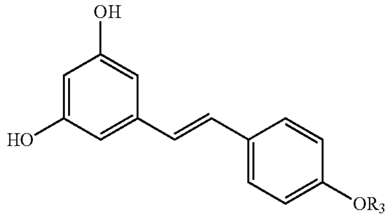
with $R_3$ selected from the group consisting preferably of:
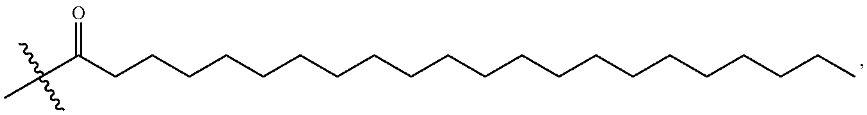
,
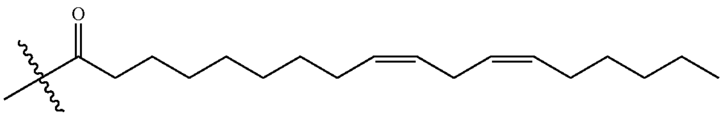
or
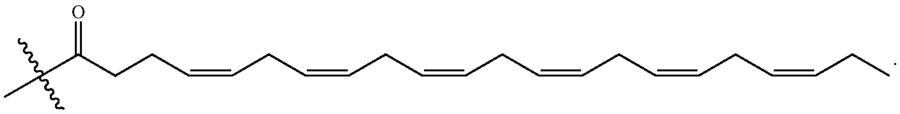
.

and more preferably

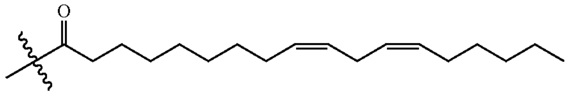 [SMILES: *C(=O)CCCCCCC/C=C\C/C=C\CCCCC]

and the disease is selected from central nervous system disorder, such as encephalitis.

In a particular and preferred embodiment, the lipophenolic compound is of formula (IIb), (IIb)

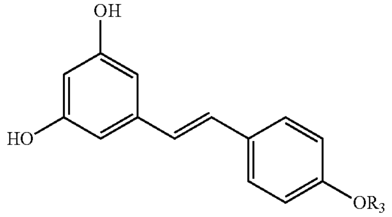

with $R_3$ selected from the group consisting preferably of:

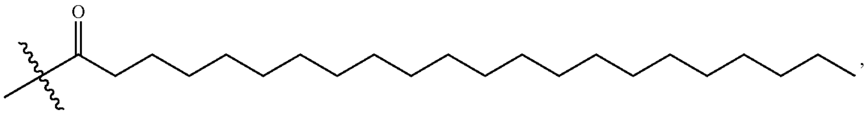

,

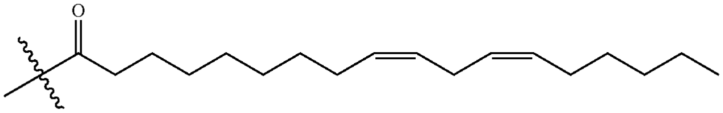

or

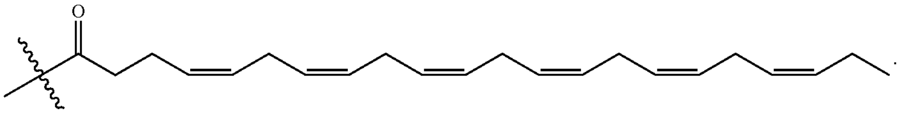

.

and more preferably

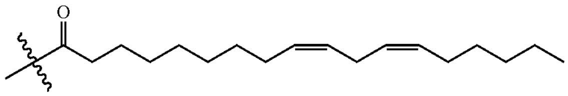 [SMILES: *C(=O)CCCCCCC/C=C\C/C=C\CCCCC]

and the disease is selected from cardiovascular diseases, in particular heart failure, cardiovascular event or stroke.

Another object of the invention is a compound of formula (IIb)

(IIb)

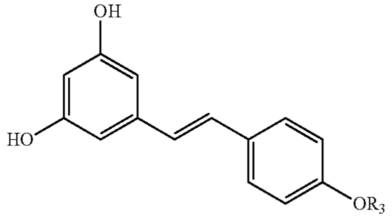

with $R_3$ selected from the group consisting of:

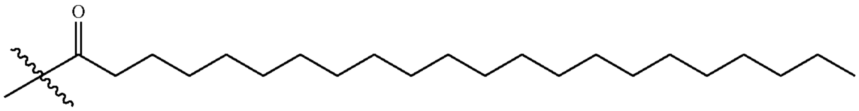

,

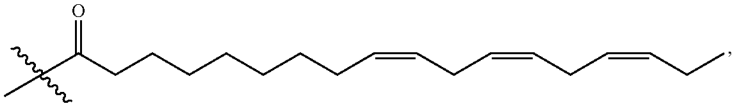

, or

-continued

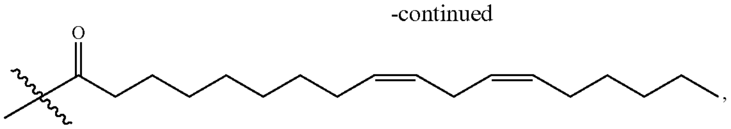

preferably

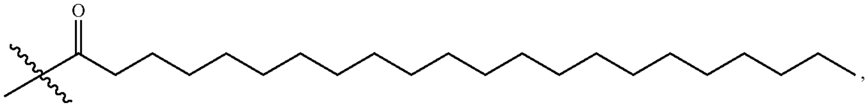

, or

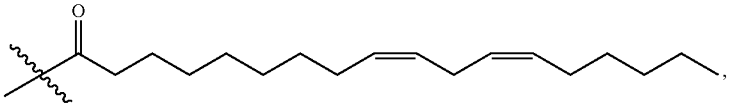

and more preferably

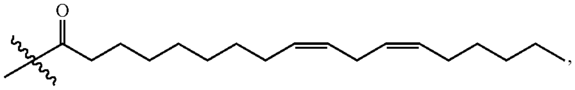 [SMILES: *C(=O)CCCCCCC/C=C\C/C=C\CCCCC]

or its pharmaceutically acceptable salts, racemates, diastereoisomers, enantiomers, or mixtures thereof.

Another object of the invention is a pharmaceutical composition comprising, in a pharmaceutically acceptable vehicle, at least one compound of formula (IIb)

(IIb)

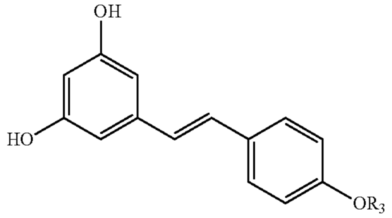

with $R_3$ selected from the group consisting of:

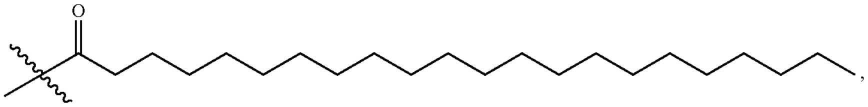

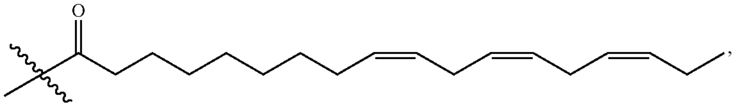

or

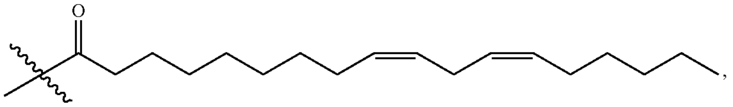

preferably

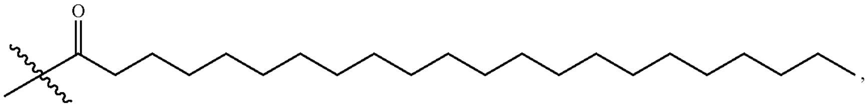

or

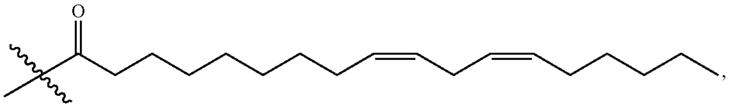

and more preferably

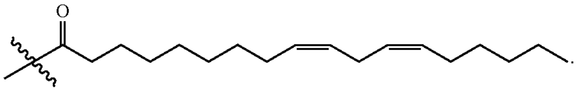 [SMILES: *C(=O)CCCCCCC/C=C\C/C=C\CCCCC]

or its pharmaceutically acceptable salts, racemates, diastereoisomers, enantiomers, or mixtures thereof.

Another object of the invention is a pharmaceutical composition or pharmaceutical kit comprising, at least one compound of formula (IIb) defined above in association with at least one additional active compound selected from the group consisting of antibiotic, antiviral, antifungal, antiparasitic, anti-inflammatory active compound and mixtures thereof.

Galenic

The lipophenolic compound of the invention may be used as such but is preferably formulated in a pharmaceutical composition comprising a pharmaceutically acceptable vehicle.

In particular, the lipophenolic compound of the invention is administered orally, intrathecally, enterally, parenterally, nutritionally, and/or intraperitoneally.

The term "pharmaceutically acceptable" according to the invention refers to compositions, carriers, diluents and reagents, capable of administration to or upon a mammal, in particular a human, without the production of undesirable physiological effects such as nausea, gastric upset and the like.

The preparation of a pharmacological composition that contains active ingredients dissolved or dispersed therein is well understood in the art and need not to be limited based on formulation. Typically, such compositions are prepared in injectable formats either as liquid solutions or suspensions; however, solid forms suitable for solution, or suspensions, in liquid prior to use can also be prepared. The preparation can also be emulsified. In particular, the pharmaceutical compositions may be formulated in solid dosage form, for example capsules, tablets, pills, powders, dragees or granules.

The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, algenic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

The lipophenolic compounds used according to the invention can be administered in a suitable formulation to humans and animals by topical or systemic administration, including oral, intrathecal, enteral, parenteral (including subcutaneous, intra-arterial, intramuscular, intravenous, intradermal), nutritional and intraperitoneal.

In a particular embodiment, the lipophenolic compound according to the invention is in a suitable formulation to humans, and in particular is administered orally, intrathecally, enterally, parenterally, nutritionally, and/or intraperitoneally.

In a preferred embodiment, the lipophenolic compound according to the invention is in a suitable formulation for oral administration.

In a particular embodiment, the lipophenolic compound according to the invention will be in a suitable form selected from:

- nano-suspension to improve their solubility and activity;
- natural deep eutectic solvent (NADES), known as having high solubilizing power, cheap components and low toxicity; NADES are composed of two or more natural metabolites (amino acids, lipids, organic amines and sugars) that when mixed together with certain ratio, forms a liquid with lower melting point than any of their components (Dai et al. 2013);
- in complex with protein to improve their solubility and bioavailability (e.g.: albumin)

In a particular and preferred embodiment, the lipophenolic compound formulated in a suitable form is a compound of formula (IIb)

(IIb)

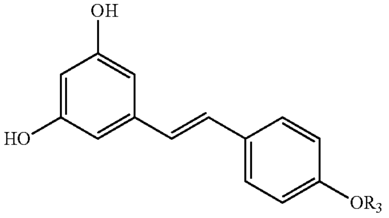

with $R_3$ selected from the group consisting preferably of:

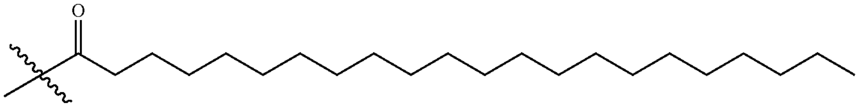

,

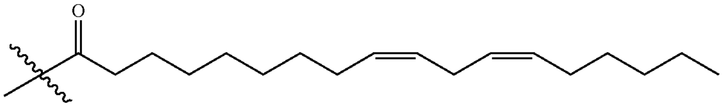

or

-continued

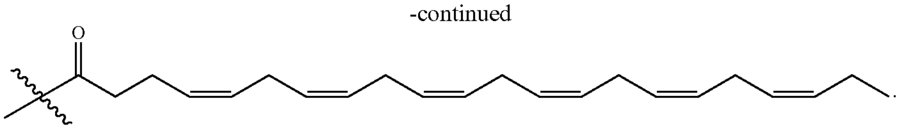

and more preferably

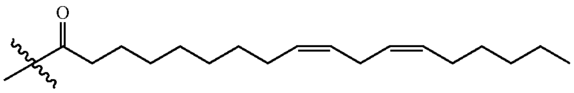 [SMILES: *C(=O)CCCCCCC/C=C\C/C=C\CCCCC]

Additional Active Compounds

In a particular embodiment, the lipophenolic compound according to the invention is associated with at least one additional active compound selected from the group consisting of antibiotic, antiviral, antifungal, antiparasitic, anti-inflammatory active compound and mixtures thereof.

The man skilled in the art may refer to compounds usually known as antibiotic, antiviral, antifungal, antiparasitic, anti-inflammatory active compound and mixtures thereof.

The additional active compound may be administered simultaneously or sequentially with the lipophenolic compound of the invention.

In a first embodiment, the additional compound is present in the same pharmaceutical composition than the lipophenolic compound.

In another embodiment, the additional compound is present in a separate compartment or composition than the pharmaceutical composition containing the lipophenolic compound.

In a particular embodiment, the lipophenolic compound formulated is a compound of formula (IIb)

(IIb)

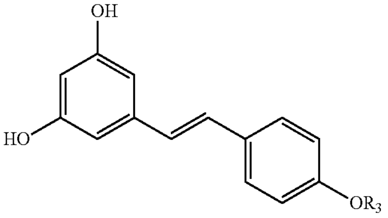

with $R_3$ selected from the group consisting preferably of:

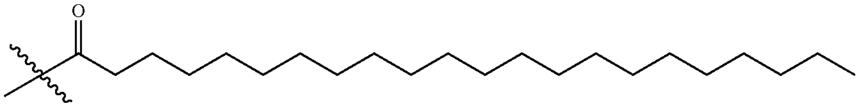

,

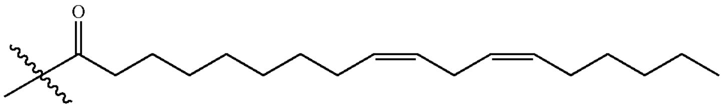

or

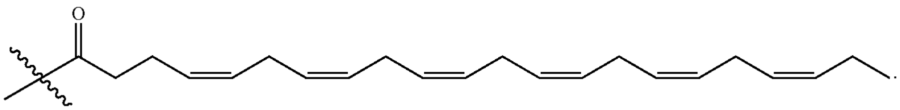

.

and more preferably

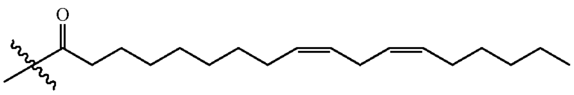 [SMILES: *C(=O)CCCCCCC/C=C\C/C=C\CCCCC]

associated with at least one additional active compound selected from the group consisting of antibiotic, antiviral, antifungal, antiparasitic, anti-inflammatory active compound and mixtures thereof.

The man skilled in the art will choose the additional active compound considering the disease or disorder to be prevented and/or treated.

In particular, for a central nervous system disorder, he may use an anti-inflammatory active compound.

In another embodiment, for viral hemorrhagic fever, he may use an antiviral compound.

Short-Term Treatment

As new MMP-9 inhibitors, the lipophenolic compounds of the invention will be used preferably not in a long-term continuous treatment, but in a discontinuous or short-term intermittent treatment administration.

By 'discontinuous or intermittent' treatment according to the invention, it means that the lipophenolic compounds are administered for a short-term period, also named 'short-term treatment', for example for 1 to 4 days, in particular for 1 day, for 2 days, for 3 days or for 4 days, preferably for 1 day or 2 days.

In a particular embodiment, the lipophenolic compound according to the invention may be administered before, during and/or after an acute disorder phase (ex: acute inflammatory phase), for a short-term treatment. The acute disorder phase may be forecasted, in a subject susceptible to be affected, by specific markers (including MMP-9) of the said disorder.

In another embodiment, the lipophenolic compound according to the invention may be administered before, during and/or after a chronic disorder phase, for a short-term treatment.

In a particular and preferred embodiment, the lipophenolic compound according to the invention is administered for a short-term treatment, for 1 to 4 days, and preferably just before or during the acute phase with a potential or clear increased vascular permeability.

The invention will be illustrated in the following non-limitative figures and examples.

FIGURES

FIG. 1: Chemical and enzymatic synthesis of 4'-Resv-$C_{22}$ or 4'-Resv-BE, 4'-Resv-DHA, 4'-Resv-LA and 4'-Resv-ALA.

Figure 2:
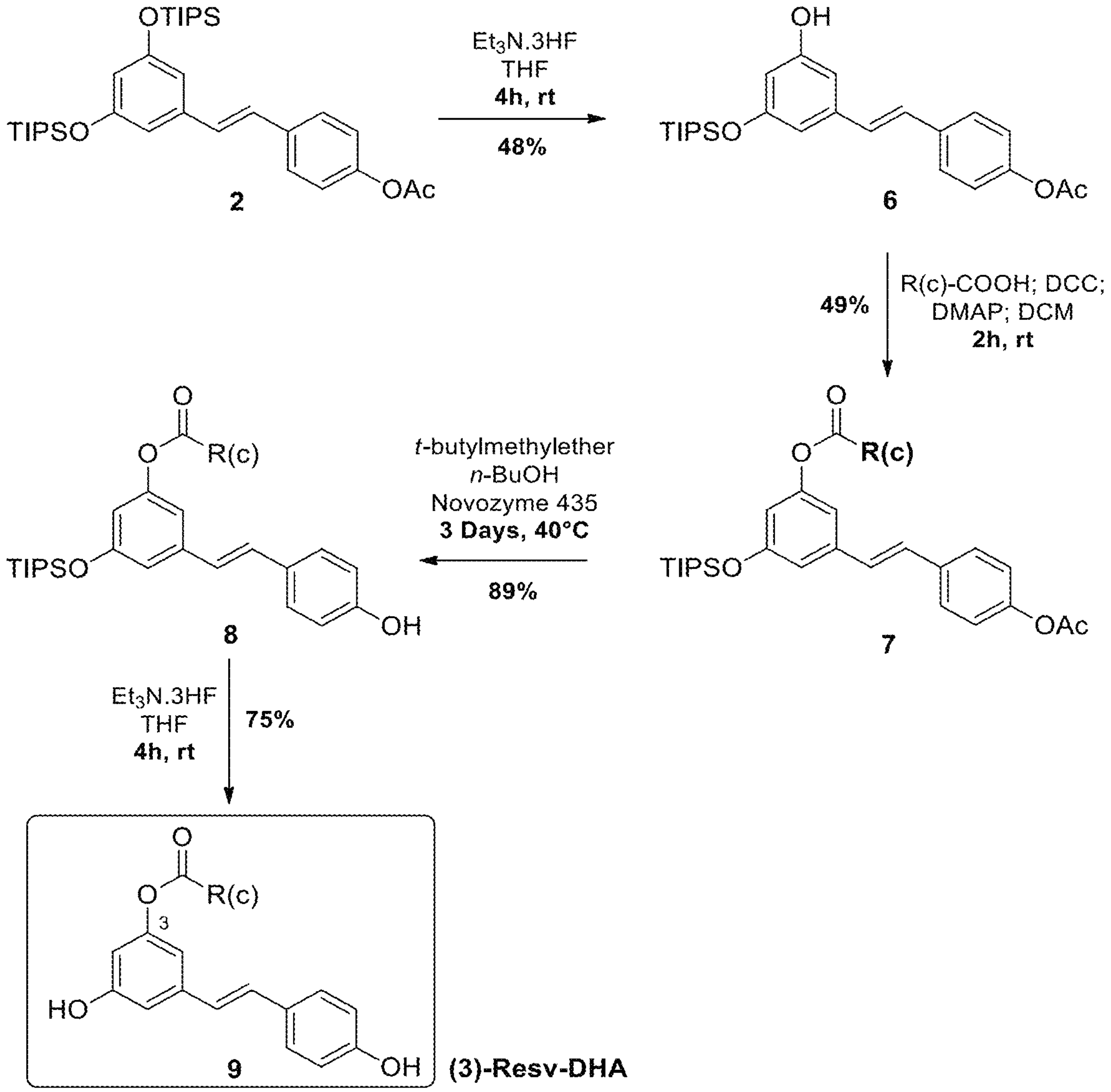

FIG. 2: Chemical and enzymatic synthesis of 3-Resv-DHA.

Figure 3:
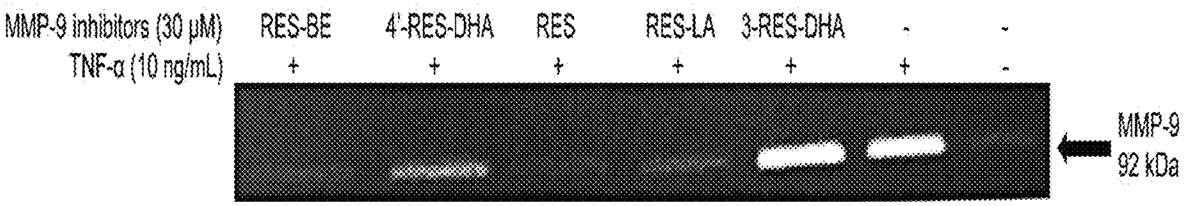

FIG. 3: Assessment of anti-MMP-9 activity of resveratrol lipophenolic derivatives.

Figure 4A:
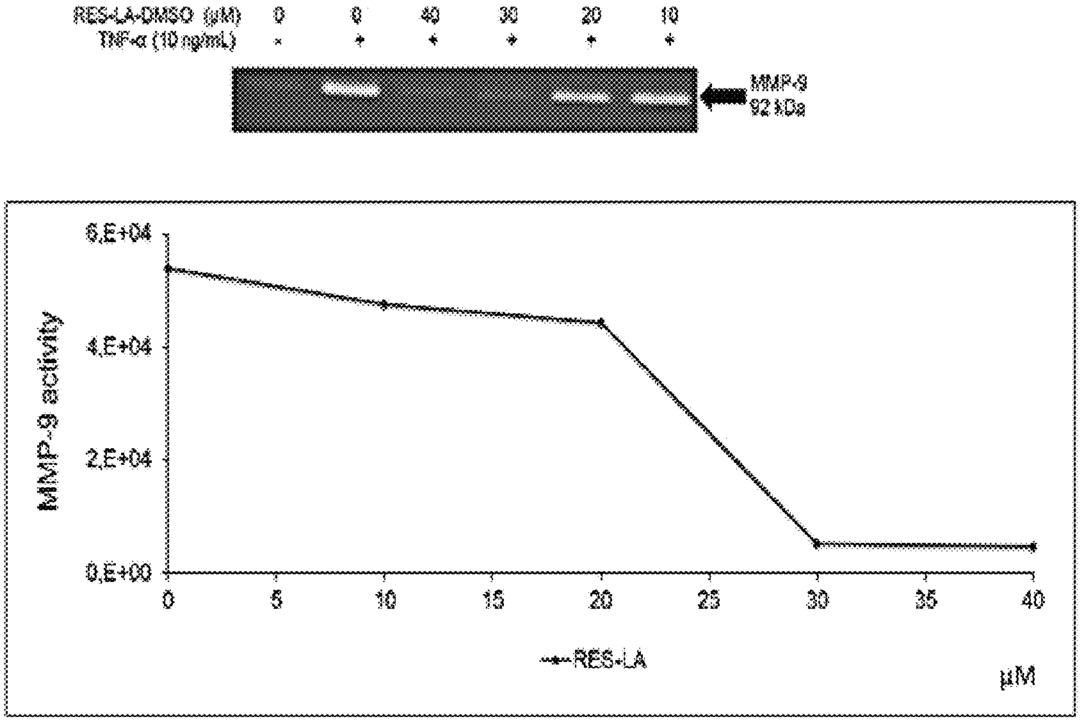
Figure 4B:
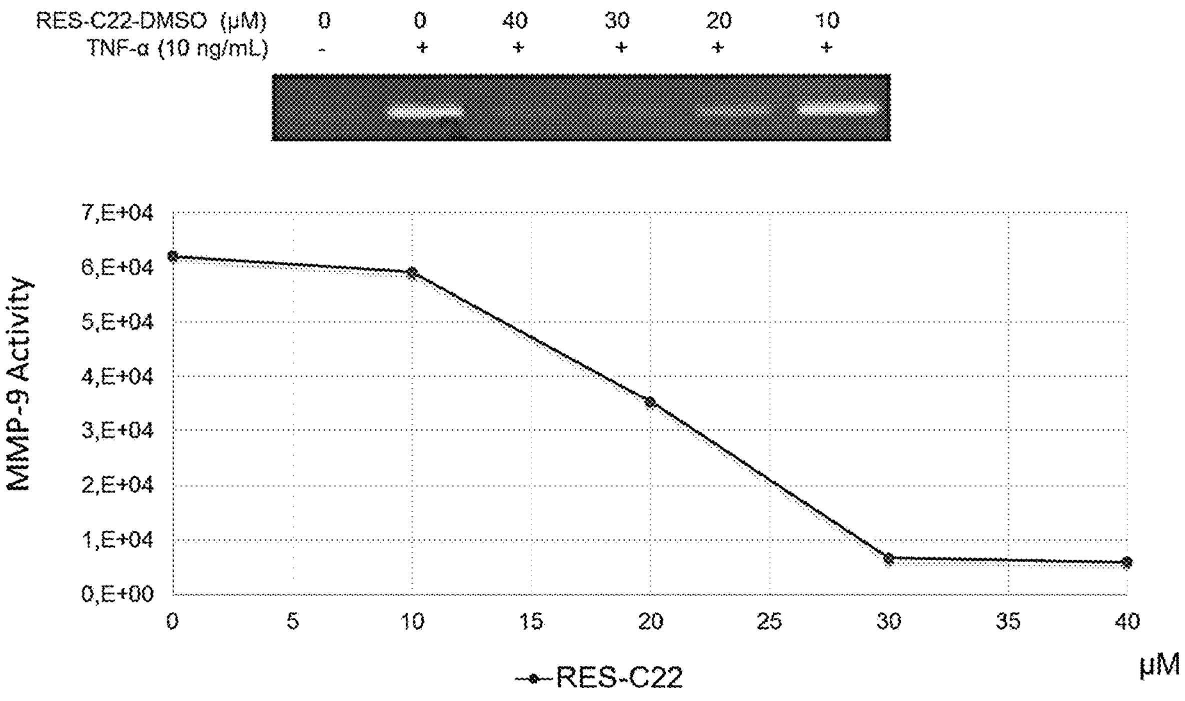

FIG. 4: Zymogram and Curve of the dose-response effect of Resv-LA (FIG. 4A) and Resv-C22 or Resv-BE (FIG. 4B) respectively on the inhibitory MMP-9 activity.

Figure 5:
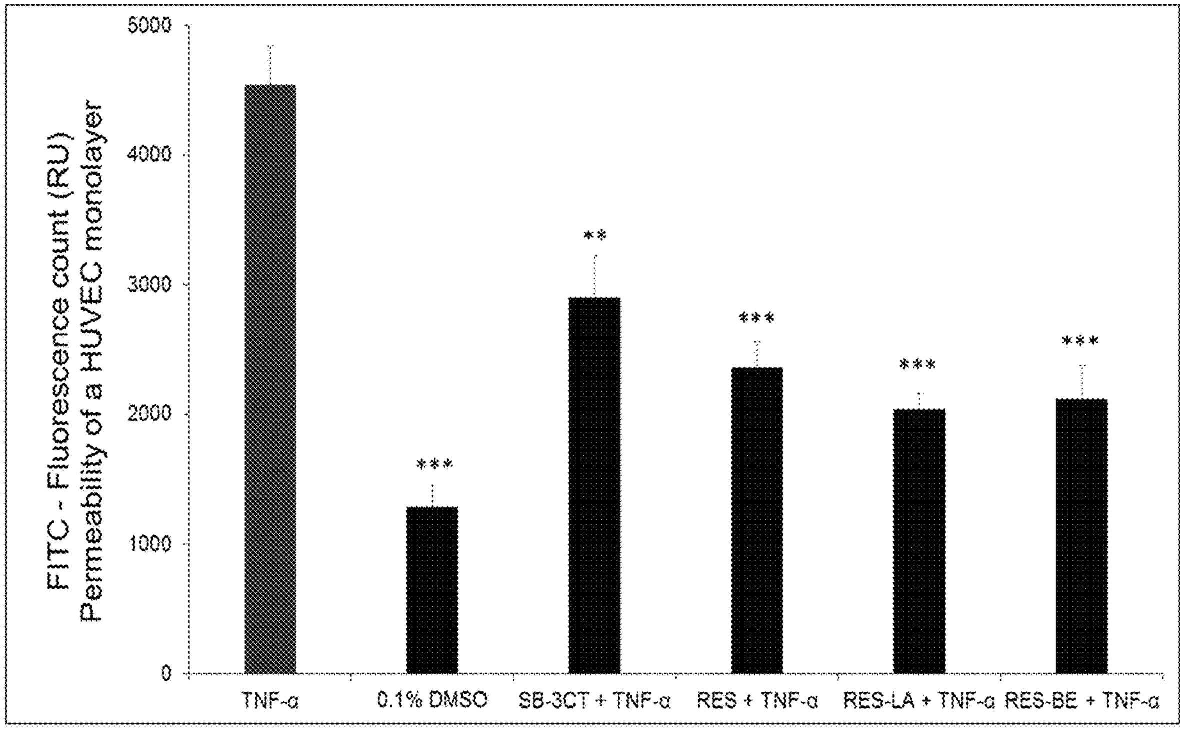

FIG. 5: Assessment of in vitro vascular permeability assay of resveratrol lipophenolic derivatives.

Figure 6A:
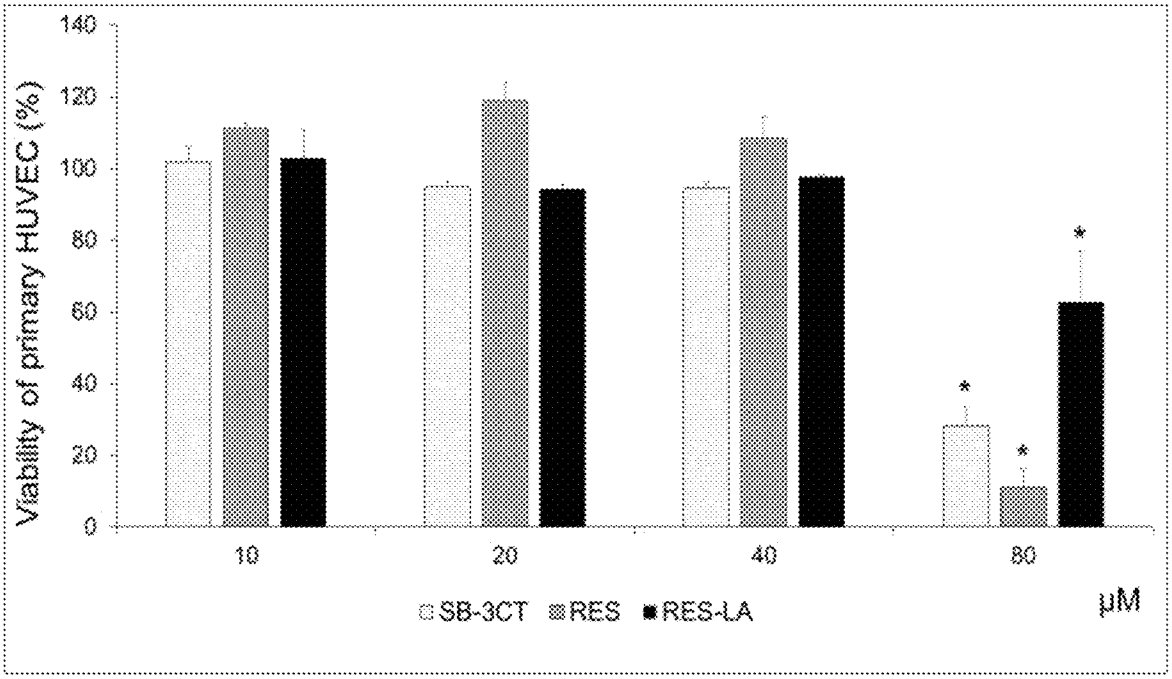
Figure 6A:
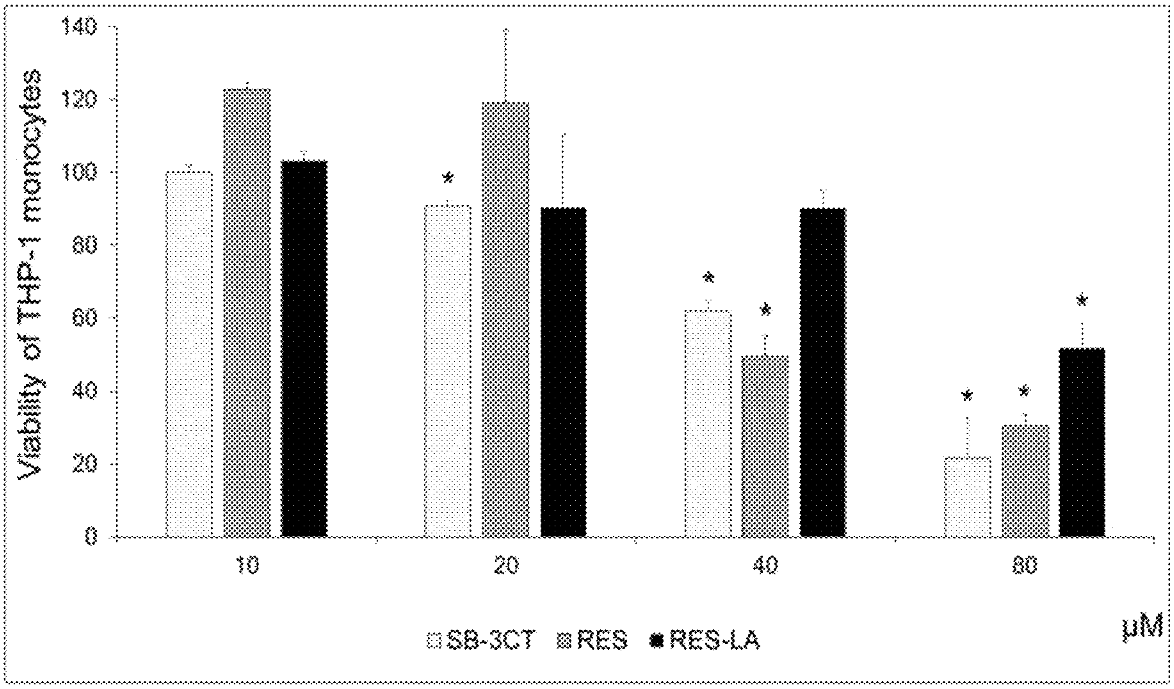
Figure 6B:
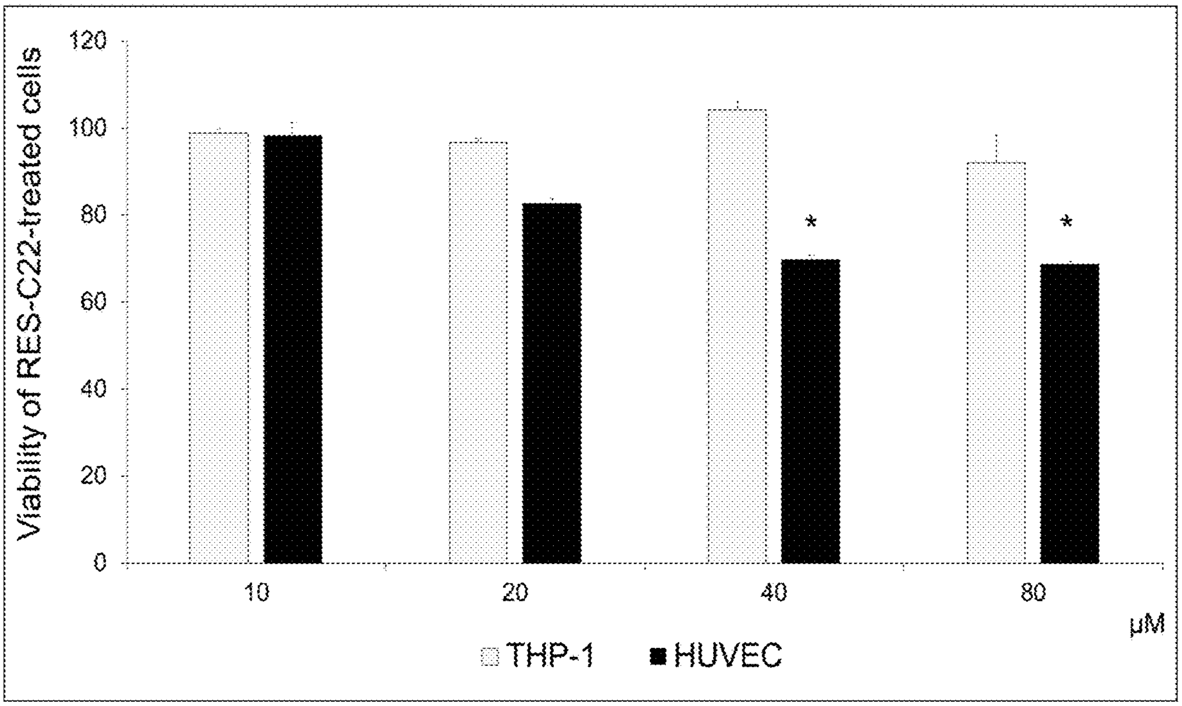

FIG. 6: Assessment of cell viability assay of Resv-LA (FIG. 6A) and Resv-C22 or Resv-BE (FIG. 6B) respectively.

Figure 7:
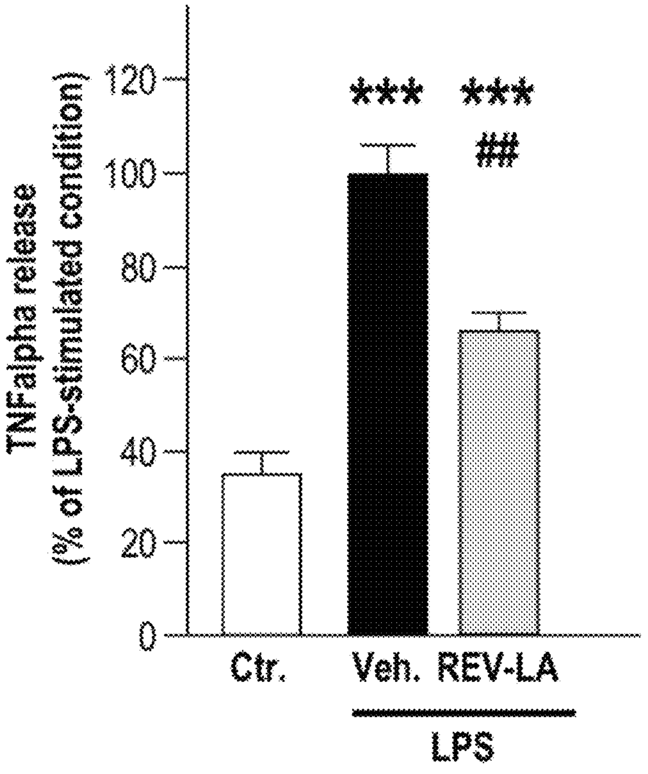

FIG. 7: Assessment of the inhibitory effect of Resv-LA (REV-LA) on TNF-α release by LPS-activated microglia.

EXAMPLES

Materials and Methods

THP-1 cells (human monocytic THP-1 cell line) were cultured in 10% heated inactivated FBS RPMI 1640 medium supplemented with penicillin G 100 units/mL and streptomycin 100 μg/mL purchased from Fisher Scientific™ (Illkirch-Graffenstaden, France).

Human umbilical vascular endothelial cells (HUVECs) were cultured in low serum (1%) EndoGro™ medium kit purchased from Merck Millipore™ (Paris, France). TNF-α was purchased from PeproTech™ (Neuilly-Sur-Seine, France).

Resveratrol has been isolated and purified from stalks of *Vitis vinifera*, Vitaceae, according to the process described by (Delaunay et al. 2002), SB-3CT #BML-E1325 (specific thiirane gelatinase inhibitor used as a reference: it blocks laminin degradation by MMP-9 so that prohibiting neuron apoptosis) was purchased from Enzo Life Sciences™ (Villeurbanne, France) and dissolved in Dimethyl sulfoxide (DMSO) Sigma-Aldrich™.

Human CD31/PECAM-1 antibody (BBA7) and Streptavidin-Fluorescein (4800-30-14) were purchased from Bio-Techne™ (Abingdon, United Kingdom), and all other chemicals used in this study are highly purified molecular grade reagents.

Example 1: Synthesis of Resveratrol Derived Lipophenols

To evaluate the activity of different lipid chains at the 4' position, Resv-C22 or Resv-BE (5a), Resv-LA (5b), Resv-DHA (5c) and Resv-ALA (5d) were synthesized using enzymatic and chemical synthesis starting from resveratrol (FIG. 1). In the first step, the supported lipase *Candida antartica* (CALB, Novozyme 435, selective of the 4' position) was used to introduce acetyl group regio-selectively at the resveratrol C4-OH position. The reaction was performed in good yield (85%) without any acetyl derivatives at the 3 or 5 positions. Hydroxyl groups at 3 and 5 positions of compound 1 were then protected by triisopropylsilyl (TIPS) protecting groups using triflate reagent (TIPS-OTf) and diisopropylethylamine (DIPEA) as a base to obtain the protected derivative 2. The acetyl group of compound 2 was deprotected with a solution of sodium methanolate (MeONa) in anhydrous methanol and resulted resveratrol-diTIPS (3) in an excellent yield of 95%. The coupling reactions between compound 3 and the difference fatty acid, docosanoic acid or behenic acid (C22), linoleic acid (LA), docosahexaenoic acid (DHA) and linolenic acid (ALA) were initiated using dicyclohexylcardodiimide and dimethylaminopyridine (DCC/DMAP) as coupling reagents to access 4a-d. Final deprotection of TIPS protecting groups by $Et_3N$-3HF in dry tetrahydrofuran (THF) yielded final lipophenols 5a-d.

In order to study the importance of the position of the lipidic part on the resveratrol structure, the synthesis of a lipidic resveratrol having the fatty acid at the 3 position was developed. Starting from the fully protected resveratrol 2, one TIPS group at the 5 position was removed using mild $Et_3N$-3HF carefully monitored by thin layer chromatography (48%, FIG. 2). Then, the mono deprotected derivative 6 was linked to the fatty acid (DHA) using DCC/DMAP. In order to preserve the ester linkage of the compound 7, the acetate group was deprotected using enzymatic lipase CALB in presence of butanol (89%) instead of MeONa solution. The final TIPS deprotection using $Et_3N$-3HF afforded the desired 3-Resv-DHA compound (9).

Experimental Part

(E)-4-(3,5-dihydroxystyryl)phenyl acetate (Compound 1)

resveratrol (2.88 g, 12.61 mmol) was dissolved in 2-methylbutan-2-ol (280 mL) and vinyl acetate (72.40 mL, 756.70 mmol) in presence of the supported lipase *Candida Antarctica* (Novozyme 435, CalB, 14.40 g). The mixture was stirred with a rotary evaporator at 40° C. during 4 days, protected from sunlight by aluminium foil. The lipase was then filtered off and washed with AcOEt (10×50 mL) and diethyl ether (2×50 mL). The filtrate obtained was concentrated under reduced pressure and the residue obtained was purified by chromatography on silica gel using solid deposit ($CH_2Cl_2$/MeOH 99/1 to 98/2) to give the 4'-O-acetyl resveratrol 1 (2.89 mg, 85%) as white solid. $R_f$($CH_2Cl_2$/MeOH 95/5) 0.3; $^1H$ NMR (500 MHz; $CD_3OD$) $\delta_H$ 7.54 (d, J=7.6 Hz, 2H, $H_{2'}$ and $H_{6'}$), 7.07 (d, J=7.6 Hz, 2H, $H_{3'}$ and $H_{5'}$), 7.04 (d, J=16.2 Hz, 1H, $H_8$), 6.97 (d, J=16.2 Hz, 1H, $H_7$), 6.49 (s, 2H, $H_2$, $H_6$), 6.21-6.19 (m, 1H, Ha), 2.27 (s, 3H, $CH_{3(OAc)}$); $^{13}C$ NMR (125 MHz; MeOD) $\delta_C$ 171.1, 159.7 (2C), 151.5, 140.6, 136.6, 130.2, 128.3, 128.3, 122.9 (2C), 122.9 106.1 (2C), 103.2, 20.9.

(E)-4-(3,5-bis((triisopropylsilyl)oxy)styryl)phenyl acetate (Compound 2)

4'-O-acetyl resveratrol 1 (3.18 g, 11.78 mmol) was dissolved in dry THF (160 mL). DIPEA (4.20 mL, 24.70 mmol) and TIPS-OTf (6.70 mL, 24.70 mmol) were added dropwise to the solution and the reaction mixture was stirred at room temperature during 4.5 h. Additional amount of DIPEA (1.0 mL, 5.90 mmol) and TIPS-OTf (1.6 mL, 5.90 mmol) were added to reach completion of the reaction. After 2.5 additional hours of reaction, the solvent was evaporated under reduced pressure. The residue obtained was dissolved in 200 mL of AcOEt and washed with water ((2×100 mL) and brine (100 mL). The organic phase was dried ($MgSO_4$) and concentrated under vacuum. The residue obtained was purified by chromatography on silica gel (pentane/AcOEt 99/1 to 70/30) to give the protected resveratrol 2 (6.85 g, 90%) as a colorless oil. $R_f$ (pentane/AcOEt 95/5) 0.5; $^1H$ NMR (500 MHz; $CDCl_3$) $\delta_H$ 7.51 (d, J=8.0 Hz, 2H, $H_{2'}$ and $H_{6'}$), 7.09 (d, J=8.0 Hz, 2H, $H_{3'}$ and $H_{5'}$), 6.98 (d, J=16.3 Hz, 1H, $H_8$), 6.92 (d, J=16.3 Hz, 1H, $H_7$), 6.65 (s, 2H, $H_2$, $H_6$), 6.37-6.36 (m, 1H, Ha), 2.31 (s, 3H, $CH_{3(OAc)}$), 1.26 (m, 6H, CH—Si), 1.12 (d, J=7.6 Hz, 36H, ($CH_3$—CH); $^{13}C$ NMR (125 MHz; $CDCl_3$) $\delta_C$ 169.7, 157.3 (2C), 150.2, 139.0, 135.3, 129.3, 127.8, 127.7 (2C), 122.0 (2C), 111.6 (2C), 111.5, 21.4, 18.2 (6C), 12.9 (12C).

(E)-4-(3,5-bis((triisopropylsilyl)oxy)styryl)phenol (Compound 3)

The protected resveratrol 2 (6.85 g, 10.59 mmol) was dissolved in dry MeOH (58 mL) and $CH_2Cl_2$ (28 mL). Sodium methoxide (191 mg, 3.53 mmol) was added to the solution and the reaction mixture was stirred at room temperature during 4.5 h. Further, 0.3 eq of NaOMe (191 mg, 3.53 mmol) was added to drive the reaction to completion. After additional 2 h, the solvent was evaporated under reduced pressure. The residue obtained was purified by chromatography on silica gel (pentane/AcOEt 96/4 to 90/10) to give the 4'-deprotected resveratrol 3 (6.04 g, 95%) as an colorless oil. $R_f$ (hexane/AcOEt 90/10) 0.41; $^1H$ NMR (500 MHz; $CD_3OD$) $\delta_H$ 7.38 (d, J=8.5 Hz, 2H, $H_{2'}$ and $H_6$), 6.95 (d, J=16.2 Hz, 1H, $H_8$), 6.84 (d, J=16.2 Hz, 1H, $H_7$), 6.77 (d, J=8.5 Hz, 2H, $H_{3'}$ and $H_5$), 6.64-6.63 (m, 2H, $H_2$, $H_6$), 6.30-6.29 (m, 1H, $H_4$), 1.30-1.22 (m, 6H, CH—Si), 1.14 (d, J=7.5 Hz, 36H, $CH_3$—CH); $^{13}C$ NMR (125 MHz; MeOD) $\delta_C$ 158.5, 158.3 (2C), 141.3, 130.1, 129.9, 129.0 (2C), 126.5, 116.5 (2C), 112.1 (2C), 111.4, 18.4 (6C), 13.9 (12C).

Description of 4'-Resv-C22 (4-Resv-BE) Series (E)-4-(3,5-bis((triisopropylsilyl)oxy)styryl)phenyl docosanoate (Compound 4a)

Compound 3 (3.00 g, 5.55 mmol) and docosanoic acid also named behenic acid (2.27 g, 6.67 mmol) were partially dissolved in dry DCM (180 mL) and the required amount of dry DMF (55 mL) was added to solubilize the acid entirely. Afterwards, DCC (1.70 g, 8.33 mmol) and DMAP (339 mg, 2.78 mmol) were added and the reaction was stirred at room temperature under argon until the conversion was completed according to TLC. After 6 h, the reaction was stored into the fridge (4° C.) to allow the formation of DCU precipitate, which was then filtered on frit. DCM (65 mL) was added to the filtrate and it was washed with water (2×150 mL) and brine (150 mL). The organic layer was dried over $MgSO_4$ and evaporated to gain 8.00 g of crude product. Purification was performed by chromatography on silica gel (pentane/EtOAc 99:1) to yield 4a (6.63 g, 76%) as a white solid.

$R_f$ (pentane/EtOAc 99:1) 0.4; $^1H$ NMR (500 MHz, $CDCl_3$): $\delta_H$ 7.50 (d, J=8.5 Hz, 2H, $H_{2'}$ and $H_{6'}$), 7.07 (d, J=8.5 Hz, 2H, $H_{3'}$ and $H_5$), 6.99 (d, J=16.0 Hz, 1H, $H_8$), 6.92 (d, J=16.0 Hz, 1H, $H_7$), 6.65 (d, J=2.0 Hz, 2H, $H_2$ and $H_6$), 6.36 (t, J=2.5 Hz, 1H, Ha), 2.56 (t, J=7.5 Hz, 2H, $CH_2$—C═O), 1.76 (quint, J=7.5 Hz, 2H, $CH_2$—$CH_2$—C═O), 1.43-1.22 (m, 42H, $\underline{CH_2}$—$CH_2$ and $\underline{CH}$—Si), 1.11 (d, J=7.5 Hz, 36H, $\underline{CH_3}$—CH), 0.89 (t, J=7.1 Hz; 3H, $\underline{CH_3}$—$CH_2$). $^{13}C$ NMR (126 MHz, $CDCl_3$) $\delta_C$ 172.4, 157.2, 157.2, 150.2, 138.9, 135.1, 129.1, 127.7, 127.5 (2C), 121.9 (2C), 111.5 (2C), 111.4, 34.6, 32.1, 29.9 (8C), 29.8, 29.8, 29.8, 29.7, 29.6, 29.5, 29.4, 29.2, 25.1, 22.8, 18.1 (6C), 14.3, 12.8 (12C).

(E)-4-(3,5-dihydroxystyryl)phenyl docosanoate (Compound 5a)

Compound 4a (3.63 g, 4.20 mmol) was dissolved in dry THF (220 mL) under argon atmosphere. Addition of $Et_3N$-3HF (4.11 mL, 25.21 mmol) was arranged via plastic syringe and the reaction was allowed to stir at room temperature and monitored by TLC (pentane/EtOAc 7:3 and 9:1). Additional equivalents of $Et_3N$-3HF were added after 3.5 h (2.06 mL, 12.61 mmol) and 6 h (2.06 mL, 12.61 mmol) of reaction. After 8 hours, the THF was evaporated under reduced pressure and the residue was dissolved in 400 mL of EtOAc, and then washed with $H_2O$ (3×200 mL) and brine (200 mL). The organic layer was dried over $MgSO_4$ and evaporated to gain 2.70 g of crude product. Purification was performed by chromatography on silica gel using solid deposit (pentane/EtOAc 7:3 to 0:1) and resulted in 503 mg (17%) of mono protected derivative and 1.82 g (79%) of compound 5a as a white solid.

$R_f$ (pentane EtOAc 7:3) 0.3; $^1H$ NMR (500 MHz, $CDCl_3$/MeOD 10:1) $\delta_H$ 7.31 (d, J=8.5 Hz, 2H, $H_{2'}$ and $H_{6'}$), 6.87 (d, J=8.5 Hz, 2H, $H_{3'}$ and $H_{5'}$), 6.84 (d, J=16.5 Hz, 1H, $H_8$), 6.74 (d, J=16.5 Hz, 1H, $H_7$), 6.34 (d, J=2.0 Hz, 2H, $H_2$ and $H_6$), 6.08 (t, J=2.0 Hz, 1H, $H_4$), 2.39 (t, J=7.0 Hz, 2H, $CH_2$—C═O), 1.57 (quint, J=7.0 Hz, 2H, $\underline{CH_2}$—$CH_2$—C═O), 1.23-1.07 (m, 36H, $\underline{CH_2}$—$CH_2$), 0.69 (t, J=6.6 Hz, 3H, $\underline{CH_3}$—$CH_2$); $^{13}C$ NMR (126 MHz, $CDCl_3$/MeOD 10:1) $\delta_C$ 172.8, 157.9 (2C), 149.8, 139.1, 135.0, 128.9, 127.3, 127.2 (2C), 121.6 (2C), 105.1 (2C), 102.1, 34.2, 31.7, 29.5 (9C), 29.4, 29.4, 29.4, 29.3, 29.2, 29.0, 28.9, 24.7, 22.5, 13.8.

Description of 4'-Resv-LA Series (9,12Z)-4-((E)-3,5-bis((triisopropylsilyl)oxy)styryl)phenyl octadeca-9,12-dienoate (Compound 4b)

Compound 3 (1.00 g, 1.67 mmol) and linoleic acid (LA; 623 mg, 2.22 mmol) were dissolved in dry DCM (40 mL). Next, DCC (573 mg, 2.78 mmol) and DMAP (113 mg, 0.93 mmol) were added to the reaction mixture which was stir at room temperature under inert atmosphere (monitored by TLC pentane/EtOAc 95:5). The reaction was terminated after 3 hours. Flask was put into the fridge (4° C.) for 1 h min to maximize the amount of DCU crystals. White DCU precipitate was then removed by filtration on frit, rinsed by a few drops of cold DCM. Filtrate was diluted by 40 mL of DCM and washed twice with water (30 mL) and once with brine (30 mL). Aqueous phases were re-extracted with 100 mL of DCM. Organic layers were collected, dried over $MgSO_4$ and evaporated. Purification by silica gel column chromatography (pentane/EtOAc 99.5/5 to 99/1) resulted in 1.10 g (74%) of compound 4b (colorless oil).

Rf (pentane/EtOAc 95:5) 0.7; $^1H$ NMR (500 MHz, $CDCl_3$): $\delta_H$ 7.79 (d, J=8.5 Hz, 2H, $H_{2'}$ and $H_{6'}$), 7.06 (d, J=8.5 Hz, 2H, $H_{3'}$ and $H_{5'}$), 6.97 (d, J=16 Hz, 1H, $H_8$), 6.91 (d, J=16 Hz, 1H, $H_7$), 6.64 (d, J=1.5 Hz, 2H, $H_2$ and $H_6$), 6.3 (t, J=1.5 Hz, 1H, $H_4$), 5.41-5.33 (m, 4H, CH═CH), 2.78 (t, J=6.5 Hz, 2H, $CH_2$ bis-allylic), 2.55 (t, J=7.5 Hz, 2H, $CH_2$—C═O), 2.07-2.03 (m, 4H, $CH_2$ allylic), 1.75 (quint, J=7.5 Hz, 2H, $\underline{CH_2}$—$CH_2$—C═O), 1.42-1.22 (m, 20H, $CH_2$—$CH_2$ and CH—Si), 1.11 (d, J=7.5 Hz, 36H, $\underline{CH_3}$—CH), 0.89 (t, J=7 Hz, 3H, $\underline{CH_3}$—$CH_2$); $^{13}C$ NMR (126 MHz, $CDCl_3$) $\delta_C$ 172.6, 157.4 (2C), 150.4, 139.1, 135.3, 130.6, 130.3, 129.3, 128.4, 128.2, 127.9, 127.7 (2C), 122.1 (2C), 111.7 (2C), 111.6, 34.8, 31.8, 29.9, 29.7, 29.5, 29.4, 29.4, 27.5, 27.5, 26.0, 25.3, 22.9, 18.2 (6C), 14.4, 13.0 (12C).

(9,12Z)-4-((E)-3,5-dihydroxystyryl)phenyl octadeca-9,12-dienoate (Compound 5b)

$Et_3N$-3HF (1.32 mL, 8.08 mmol) was added via plastic syringe to a solution of Compound 4b (1.08 g, 1.35 mmol) dissolved in dry THF (60 mL) The reaction was stirred at room temperature under argon. Further equivalents of $Et_3N$-3HF (2×0.66 mL, 2×4.04 mmol) were added at four and six hours of reaction time. Reaction was terminated after another two hours (reaction time 8 h, monitored by TLC pentane/EtOAc 7:3 and 9:1). Reaction media was evaporated and the residue was dissolved in EtOAc (120 mL). Organic phases was washed with $H_2O$ (3×60 mL) and brine (60 mL), dried over $MgSO_4$, filtered and evaporated under reduced pressure. Crude product was purified by column chromatography on silica gel (pentane/EtOAc 7:3 to 6:4) to obtain 5b (546 mg, 83%) as a white solid.

$R_f$ (pentane/EtOAc 7:3) 0.3; $^1$H NMR (500 MHz, $CDCl_3$) $\delta_H$ 7.34 (d, J=8.5 Hz, 2H, $H_{2'}$ and $H_{6'}$), 7.00 (d, J=8.5 Hz, 2H, $H_{3'}$ and $H_{5'}$), 6.79 (d, J=16.5 Hz, 1H, $H_8$), 6.70 (d, J=16.5 Hz, 1H, $H_7$), 6.40 (d, J=2.0 Hz, 2H, $H_2$ and $H_6$), 6.23 (t, J=2.0 Hz, 1H, $H_4$), 5.99 (Br, 2H, OH), 5.41-5.32 (m, 4H, CH═CH), 2.77 (t, J=6.5 Hz, 2H, $CH_2$ bis-allylic), 2.56 (t, J=7.5 Hz, 2H, $CH_2$—C═O), 2.06-2.03 (m, 4H, $CH_2$ allylic), 1.75 (quint, J=7.5 Hz, 2H, $\underline{CH_2}$—$CH_2$—C═O), 1.42-1.25 (m, 14H, $CH_2$—$CH_2$), 0.88 (t, J=7 Hz, 3H, $\underline{CH_3}$—$CH_2$); $^{13}$C NMR (126 MHz, $CDCl_3$) $\delta_C$ 173.5, 157.0 (2C), 150.1, 139.7, 135.1, 130.4, 130.2, 128.4, 128.2, 128.2, 128.0, 127.7 (2C), 121.8 (2C), 106.3 (2C), 102.6, 34.6, 31.7, 29.7, 29.5, 29.3, 29.3, 29.2, 27.3, 27.3, 25.7, 25.0, 22.7, 14.2.

Description of 4'-Resv-DHA Series (4c and 5c)

The synthesis of Resv-DHA is described in the publication Crauste et al. (2014).

(4,7,10,13,16,19 Z)-4-((E)-3,5-bis(triisopropylsilyloxy)styryl)phenyl docosa-4,7,10,13,16,19-hexaenoate (Compound 4c)

Coupling of the di-protected resveratrol 3 (103 mg, 0.18 mmol) and DHA (67 mg, 0.20 mmol) was performed with the general procedure and afforded 4c (130 mg, 80%) as an uncolored oil after purification on silicagel chromatography (hexane/AcOEt 99/1).

$R_f$ (hexane/AcOEt 95/5) 0.73; $^1$H NMR (500 MHz; $CDCl_3$) $\delta_H$ 7.50 (d, J=8.5 Hz, 2H, $H_{2'}$ and $H_{6'}$), 7.07 (d, J=8.4 Hz, 2H, $H_{3'}$ and $H_5$), 6.98 (d, J=16.5 Hz, 1H, $H_8$), 6.92 (d, J=16.5 Hz, 1H, $H_7$), 6.64 (d, J=2.3 Hz, 2H, $H_2$, $H_6$), 6.36 (t, J=2.3 Hz 1H, $H_4$), 5.50-5.29 (m, 12H, CH═CH), 2.90-2.80 (m, 10H, $CH_2$ bis-allylic), 2.64 (t, J=7.0 Hz, 2H, $CH_2$—C═O), 2.55-2.51 (m, 2H, $CH_2$ allylic), 2.08 (quint, J=7.0 Hz, 2H, $CH_2$ allylic), 1.29-1.22 (m, 6H, CH—Si), 1.12 (d, J=7.5 Hz, 36H, $(CH_3)_2C$); 0.98 (t, J=7.5 Hz, 3H, $CH_3$); $^{13}$C NMR (125 MHz; $CDCl_3$) $\delta_C$ 171.8, 157.4, 150.4, 139.1, 135.3, 132.3, 130.0, 129.3, 128.9, 128.7, 128.6, 128.6, 128.4, 128.4, 128.3, 128.2, 127.9, 127.8, 127.7, 127.3, 122.0, 111.7, 111.6, 34.6, 25.9, 25.9, 25.8, 23.1, 20.9, 18.2, 14.6, 13.0

(4,7,10,13,16,19 Z)-4-((E)-3,5-dihydroxyphenylstyryl)phenyl docosa-4,7,10,13,16,19-hexaenoate (Compound 5c)

deprotection of the protected DHA-resveratrol 4c (142 mg, 0.17 mmol) was performed with the general procedure and afforded 5c (55 mg, 61%) as white solid after 7 h of reaction and purification on silicagel chromatography (hexane/AcOEt 95/5 to 70/30).

$R_f$ (hexane/AcOEt 70/30)=0.22; $^1$H NMR (500 MHz; $CDCl_3$) $\delta_H$ 7.45 (d, J=8.6 Hz, 2H, $H_{2'}$ and $H_{6'}$), 7.07 (d, J=8.5 Hz, 2H, $H_{3'}$ and HO, 6.95 (d, J=16.2 Hz, 1H, $H_8$), 6.85 (d, J=16.2 Hz, 1H, $H_7$), 6.51 (d, J=2.1 Hz, 2H, $H_2$, $H_6$), 6.26 (t, J=2.1 Hz, 1H, $H_4$), 5.52-5.29 (m, 12H, $CH_2$ bis-allylic), 5.13 (br, 2H, OH), 2.90-2.80 (m, 10H, $CH_2$ allylic), 2.66 (t, J=7.4 Hz, 2H, $CH_2$—C═O), 2.52-2.56 (m, 2H, $CH_2$ allylic), 2.08 (quint, J=7.8 Hz, 2H, $CH_2$ allylic), 0.98 (t, J=7.3 Hz, 3H, $CH_3$); $^{13}$C NMR (125 MHz; $CDCl_3$) $\delta_C$ 172.3, 157.3, 150.4, 140.0, 135.2, 132.4, 130.1, 128.9, 128.7, 128.6, 128.6, 128.6, 128.5, 128.4, 128.4, 128.3, 128.2, 127.8, 127.7, 127.3, 122.1, 106.4, 102.7, 34.6, 25.9, 25.8, 23.1, 20.9, 14.6

Description 4'-Resv-ALA Series

(9,12, 15Z)-4-((E)-3,5-bis((triisopropylsilyl)oxy)styryl)phenyl octadeca-9,12,15-trienoate (Compound 4d)

A solution of linolenic acid (ALA; 56 mg, 0.20 mmol) in dry DCM (2.50 mL) was added to the protected resveratrol 3 (100 mg, 0.18 mmol) in solution in DCM (2.50 mL). DCC (42 mg, 0.20 mmol) and DMAP (6 mg, 0.05 mmol) were added to the reaction mixture and the solution was left to stir at room temperature under inert atmosphere during 2 h (monitored by TLC pentane/EtOAc 95:5). Flask was put into the fridge (4° C.) for 1 h to maximize the amount of DCU crystals. White DCU precipitate was then removed by filtration on frit, rinsed by a few drops of cold DCM. Filtrate was diluted by 10 mL of DCM and washed twice with water (10 mL) and once with brine (10 mL). The organic layer was dried over $MgSO_4$ and evaporated. Purification by silica gel column chromatography (pentane/EtOAc 99.5/5 to 99/1) resulted in 115 mg (76%) of compound 4d as a colorless oil.

Rf (pentane/EtOAc 95:5) 0.5; $^1$H NMR (500 MHz, $CDCl_3$): $\delta_H$ 7.50 (d, J=8.5 Hz, 2H, $H_{2'}$ and HO, 7.07 (d, J=8.5 Hz, 2H, $H_{3'}$ and HO, 6.98 (d, J=16.5 Hz, 1H, $H_8$), 6.92 (d, J=16.5 Hz, 1H, $H_7$), 6.65 (d, J=2.5 Hz, 2H, $H_2$ and $H_6$), 6.36 (t, J=2.5 Hz, 1H, Ha), 5.39-5.36 (m, 6H, CH═CH), 2.82 (t, J=6.5 Hz, 4H, $CH_2$ bis-allylic), 2.56 (t, J=7.5 Hz, 2H, $CH_2$—C═O), 2.10-2.06 (m, 4H, $CH_2$ allylic), 1.75 (quint, J=7.5 Hz, 2H, $\underline{CH_2}$—$CH_2$—C═O), 1.43-1.21 (m, 14H, $CH_2$—$CH_2$ and CH—Si), 1.11 (d, J=7.5 Hz, 36H, $\underline{CH_3}$—CH), 0.89 (t, J=7 Hz, 3H, $\underline{CH_3}$—$CH_2$); $^{13}$C NMR (126 MHz, $CDCl_3$) $\delta_C$ 172.3, 157.2, 150.2, 138.9, 135.1, 132.1, 132.1, 130.4, 129.1, 128.4, 128.4, 127.9, 127.7, 127.5 (2C), 127.2, 121.9 (2C), 111.5 (2C), 111.4, 34.5, 29.7, 29.3, 29.2, 29.2, 27.3, 25.7, 25.6, 25.0, 20.7, 18.1 (6C), 14.4, 12.8 (12C).

(9, 12, 15Z)-4-((E)-3,5-dihydroxystyryl)phenyl octadeca-9,12-dienoate (Compound 5d)

$Et_3N$-3HF (134 µl, 0.82 mmol) was added via plastic syringe to a solution of ALA-resveratrol 4d (110 mg, 0.14 mmol) dissolved in dry THF (6 mL). Further equivalents of $Et_3N$-3HF (2×70 µL, 2×0.41 mmol) were added at four and six hours of reaction time. Reaction was terminated after another two hours (reaction time 8 h, monitored by TLC pentane/EtOAc 7:3 and 9:1). Reaction media was evaporated and the residue was dissolved in EtOAc (20 mL) and then washed with $H_2O$ (3×20 mL) and brine (20 mL). Organic phase was dried over $MgSO_4$, filtered and evaporated under reduced pressure. Crude product was purified by column chromatography on silica gel (cyclohexane/AcOEt 80/20) and afforded Resv-ALA 5d (57 mg, 84%) as white solid.

Rf (pentane/EtOAc 7/3) 0.3; $^1H$ NMR (500 MHz, $CDCl_3$): $\delta_H$ 7.38 (d, J=8.5 Hz, 2H, $H_{2'}$ and HO, 7.02 (d, J=8.5 Hz, 2H, $H_{3'}$ and HO, 6.84 (d, J=16.5 Hz, 1H, $H_8$), 6.75 (d, J=16.5 Hz, 1H, $H_7$), 6.43 (d, J=2.0 Hz, 2H, $H_2$ and $H_6$), 6.23 (t, J=2.0 Hz, 1H, Ha), 5.41-5.32 (m, 6H, CH=CH), 2.81 (t, J=6.0 Hz, 4H, $CH_2$ bis-allylic), 2.57 (t, J=7.5 Hz, 2H, $CH_2$—C=O), 2.11-2.04 (m, 4H, $CH_2$ allylic), 1.75 (quint, J=7.5 Hz, 2H, $\underline{CH_2}$—$CH_2$—C=O), 1.42-1.30 (m, 8H, $CH_2$—$CH_2$), 0.97 (t, J=7.5 Hz, 3H, $\underline{CH_3}$—$CH_2$); $^{13}C$ NMR (126 MHz, $CDCl_3$) $\delta_C$ 173.3, 157.0 (2C), 150.1, 139.7, 135.0, 132.1, 130.4, 128.4, 128.4, 128.4, 128.2, 127.9 (2C), 127.7, 127.2, 121.9 (2C), 106.3 (2C), 102.6, 34.6, 29.7, 29.3, 29.2, 26.2, 27.3, 25.7, 25.6, 25.0, 20.7, 14.4.

Description 3-Resv-DHA Series (E)-4-(3-hydroxy-5-((triisopropylsilyl)oxy)styryl) phenyl acetate (Compound 6)

$Et_3N$-3HF (554 μL, 3.40 mmol) was added dropwise via plastic syringe to a solution protected resveratrol 2 (1.00 g, 1.70 mmol) dissolved in dry THF (60 mL). The reaction was stirred at room temperature during 3 h. AcOEt (60 mL) was added to the mixture and the organic layer was washed with water (20 mL) and brine (20 mL). The organic phase was dried on $MgSO_4$ and concentrated under reduced pressure. The residue obtained was purified by chromatography on silica gel (cyclohexane/AcOEt 95/5 to 80/20) to give the mono-protected resveratrol 6 (350 mg, 48%) as a white solid. The di-deprotected resveratrol was isolated in 26% as a white solid (118 mg).

$R_f$ (Hexane/AcOEt 70/30) 0.6; 1H NMR (500 MHz, $CDCl_3$) $\delta_H$ 7.46 (d, J=8.5 Hz, 2H, $H_{2'}$ and $H_{6'}$), 7.07 (d, J=8.5 Hz, 2H, $H_{3'}$ and $H_{5'}$), 6.93 (d, J=16.5 Hz, 1H, $H_8$), 6.86 (d, J=16.5 Hz, 1H, $H_7$), 6.59 (t, J=1.5 Hz, 1H, $H_2$), 6.51 (s, 1H, $H_4$), 6.32 (t, J=2.0 Hz, 1H, $H_6$), 5.55 (Br, 1H, OH), 2.32 (s, 3H, $CH_3$—CO), 1.32-1.23 (m, 3H, CH—Si), 1.12 (d, J=7.0 Hz, 18H, $\underline{CH_3}$—CH); $^{13}C$ NMR (126 MHz, $CDCl_3$) $\delta_C$ 170.2, 157.5, 156.9, 150.1, 139.2, 135.2, 128.9, 127.9, 127.6 (2C), 121.8 (2C), 111.3, 107.0, 106.3, 21.3, 18.1 (3C), 12.8 (6C).

(4,7,10,13,16,19Z)-3-((E)-4-acetoxystyryl)-5-((triisopropylsilyl)oxy)phenyl docosa-4,7,10,13,16,19-hexaenoate (Compound 7)

Compound 6 (470 mg, 1.1 mmol) and DHA (397 mg, 1.2 mmol) were dissolved in dry DCM (20 mL) under argon. Then, DCC (250 mg, 1.21 mmol) and DMAP (13 mg, 0.1 mmol) were added to the reaction mixture and the solution was stirred at room temperature under inert atmosphere during 2 h (monitored by TLC pentane/EtOAc 90:10). The reaction was put into the fridge (4° C.) for 1 h to maximize the amount of DCU crystals. White DCU precipitate was then removed by filtration on frit, rinsed by a few drops of cold DCM. Filtrate was diluted by 20 mL of DCM and washed twice with water (15 mL) and once with brine (15 mL). Aqueous phase was re-extracted with 50 mL of DCM. Organic layers were collected, dried over $MgSO_4$ and evaporated. Purification on silica gel chromatography (cyclohexane/AcOEt 98/2) afforded compound 7 (391 mg, 49%) as a white solid.

$R_f$ (Hexane/AcOEt 90/10) 0.5; $^1H$ NMR (500 MHz, $CDCl_3$) $\delta_H$ 7.49 (d, J=8.7 Hz, 2H, $H_{2'}$ and $H_6$), 7.08 (d, J=8.7 Hz, 2H, $H_{3'}$ and $H_{5'}$), 7.00 (d, J=16.2 Hz, 1H, $H_8$), 6.93 (d, J=16.2 Hz, 1H, $H_7$), 6.84 (t, J=2.0 Hz, 2H, $H_2$ and $H_6$), 6.53 (t, J=2.0 Hz, 1H, $H_4$), 5.50-5.28 (m, 12H, CH=CH), 2.89-2.79 (m, 10H, $CH_2$ bis-allylic), 2.63-2.60 (m, 2H, $CH_2$—C=O), 2.56-2.50 (m, 2H, $CH_2$ allylic), 2.30 (s, 3H, $CH_3$—C=O), 2.10-2.04 (m, 2H, $CH_2$ allylic), 1.30-1.23 (m, 3H, CH—Si), 1.12 (d, J=7.3, 18H, $\underline{CH_3}$—CH), 0.97 (t, J=7.5, 3H, $\underline{CH_3}$—$CH_2$); $^{13}C$ NMR (126 MHz, $CDCl_3$) $\delta_C$ 171.4, 169.5, 157.1, 151.8, 150.3, 139.2, 134.9, 132.1, 129.8, 128.7, 128.7, 128.5, 128.4, 128.4, 128.3, 128.2, 128.2, 128.1, 128.0, 127.7, 127.6 (2C), 127.1, 121.9 (2C), 115.8, 112.9, 112.3, 34.4, 25.8 (2C), 25.7, 25.7, 25.6, 22.9, 21.3, 20.7, 18.0 (3C), 14.4, 12.7 (6C).

(4,7,10,13,16,19Z)-3-((E)-4-hydroxystyryl)-5-((triisopropylsilyl)oxy)phenyl docosa-4,7,10,13,16,19-hexaenoate (Compound 8)

The protected DHA-resveratrol 7 (345 mg, 0.47 mmol) was dissolved in t-buthylmethylether (55 mL) and n-BuOH (2 mL). The supported lipase *Candida Antarctica* (Novozyme 435, CalB, 345 mg) was added to the solution and the mixture was stirred at 40° C. during 3 days. The lipase was filtered off and washed with 5×30 mL of AcOEt and 2×30 mL of diethyl ether. The filtrate was concentrated under reduced pressure and the residue obtained was purified by chromatography on silica gel (cyclohexane/AcOEt 95/5 to 90/10) to give the compound 8 (291 mg, 89%) as a yellow oil.

$R_f$ (Hexane/AcOEt 90/10) 0.55; $^1H$ NMR (500 MHz, $CDCl_3$) $\delta_H$ 7.37 (d, J=8.6 Hz, 2H, $H_{2'}$ and $H_{6'}$), 6.96 (d, J=16.2 Hz, 1H, $H_8$), 6.85-6.79 (m, 5H, $H_{3'}$, $H_{5'}$, $H_2$, $H_6$ and $H_7$), 6.50 (t, J=2.1 Hz, 1H, $H_4$), 5.48-5.28 (m, 12H, CH=CH), 2.89-2.79 (m, 10H, $CH_2$ bis-allylic), 2.63-2.60 (m, 2H, $CH_2$—C=O), 2.56-2.50 (m, 2H, $CH_2$ allylic), 2.10-2.04 (m, 2H, $CH_2$ allylic), 1.30-1.24 (m, 3H, CH—Si), 1.11 (d, J=7.4 Hz, 18H, $\underline{CH_3}$—CH), 0.97 (t, J=7.5 Hz, 3H, $\underline{CH_3}$—$CH_2$); $^{13}C$ NMR (126 MHz, $CDCl_3$) $\delta_C$ 171.5, 157.0, 155.5, 151.8, 139.7, 132.2, 130.1, 129.8, 129.2, 128.7, 128.5, 128.4, 128.4, 128.2, 128.2, 128.2 (2C), 128.1, 128.0, 127.7, 127.2, 126.0, 115.7 (2C), 115.5, 112.5, 112.1, 34.5, 25.8 (2C), 25.8, 25.8, 25.7, 22.9, 20.7, 18.1 (3C), 14.4, 12.8 (6C).

(4,7,10,13,16,19Z)-3-hydroxy-5-((E)-4-hydroxystyryl)phenyl docosa-4,7,10,13,16,19-hexaenoate (Compound 9)

$Et_3N$-3HF (232 μl, 1.41 mmol) was added via plastic syringe to a solution of DHA-resveratrol 8 (330 mg, 0.47 mmol) dissolved in dry THF (20 mL) The reaction was stirred at room temperature under argon during 4 h30. TLC monitoring was carried out using pentane/EtOAc (7:3 and 9:1) to observe the desired product formation and the departure of starting material respectively. Reaction media was evaporated and the residue was dissolved in EtOAc (20 mL) and then washed with $H_2O$ (20 mL) and brine (20 mL). Organic phase was dried over $MgSO_4$, filtered and evaporated. Crude product was purified by column chromatography on silica gel (Cyclohexane/AcOEt 80/20) and afforded 3-Resv-DHA 9 (191 mg, 75%) as a white solid $R_f$ (Hexane/AcOEt 70/30) 0.33; $^1H$ NMR (500 MHz, $CDCl_3$) $\delta_H$ 7.34 (d, J=8.6, 2H, $H_{2'}$ and $H_6$), 6.95 (d, J=16.2, 1H, $H_8$), 6.83-6.73 (m, 5H, $H_{3'}$, $H_{5'}$, $H_2$, $H_6$ and $H_7$), 6.46 (t, J=2.1, 1H, $H_4$), 5.51-5.28 (m, 12H, CH═CH), 5.13 (br, 1H, OH), 5.09 (br, 1H, OH), 2.89-2.79 (m, 10H, $CH_2$ bis-allylic), 2.65-2.62 (m, 2H, $CH_2$—C═O), 2.58-2.51 (m, 2H, $CH_2$ allylic), 2.10-2.03 (m, 2H, $CH_2$ allylic), 0.97 (t, J=7.5, 3H, $\underline{CH_3}$—$CH_2$); $^{13}C$ NMR (126 MHz, $CDCl_3$) $\delta_H$ 172.0, 156.6, 155.6, 151.8, 140.3, 132.2, 129.9, 129.9, 129.6, 128.7, 128.5, 128.4, 128.4, 128.2 (2C), 128.2, 128.2, 128.1, 128.0, 127.5, 127.1, 125.5, 115.8 (2C), 111.9, 110.9, 108.1, 34.5, 25.8 (2C), 25.8, 25.7, 25.6, 22.9, 20.7, 14.4.

Example 2: Effect of Lipophenolic Derivative of Resveratrol on MMP-9 Activity THP-1 cells were seeded ($3\times10^5$ cell/well) in 24-well plate with 10 ng/mL TNF-α with or without 30 μM of resveratrol derivatives dissolved in DMSO. After 24 hours incubation at 37° C., supernatant was collected and tested on zymography. Gel bands demonstrates MMP-9 activity of activated THP-1 cell line in presence of resveratrol lipophenolic derivatives.

Assessment of MMP-9 Activity in THP-1 Cell Line

Low-serum (1%) RPMI-1640 medium was used for the assessment of MMP-9 activity on TNF-alpha activated THP-1 cell line $3\times10^6$ cell/mL. Firstly, resveratrol and its derived lipophenolic compounds were dissolve in DMSO, and incubated at a final concentration of 30 μM with 10 ng/mL TNF-alpha treated THP-1 in $CO_2$ incubator chamber for 24 hours at 37° C. After incubation, cell suspension was centrifuged at 1200 r.p.m for five minutes, supernatant was recovered and stored at −80° C. for zymogram analysis.

Zymogram

The anti MMP-9 activity was assessed using gelatin zymography. In brief, the collected supernatants were loaded on 10% SDS-polyacrylamide gel electrophoresis (PAGE) supplemented with 1% gelatin without reducing agents. After separation, gels were washed three times with 2.5% Triton X-100 and incubated with gelatinase buffer (NaCl 200 mM, Tris Base 50 mM, CaCl2) 5 mM and ZnCl2 0.25 mM; pH 7.5), for 24 hr at 37° C. on an orbital shaker at 100 r.p.m/min. Gels were further stained for one hour with Commassie Blue-staining solution (0.025% Commassie Blue, 40% methanol and 10% acetic acid) followed by destaining with 20% methanol and 10% glacial acetic acid solution until the clear bands appearance. Gels were photographed and analyzed by GelAnalyzer 2010a™ software.

The results are presented in FIG. 3, showing that Resv-LA, Resv-C22 (Resv-BE), and to a lesser extent 4'-Resv-DHA, demonstrated inhibition of MMP9-activity in TNF-alpha-activated THP-1 monocytes (FIG. 3). While 4'-Resv-DHA reduced MMP-9 activity at 30 μM, its regio-isomer, having the lipid chain linked with the hydroxyl group in position 3 of resveratrol, the 3-Resv-DHA (FIG. 2), was not active at the same concentration.

Resv-LA and Resv-C22 (Resv-BE) have demonstrated interesting inhibition of activity of MMP-9 (FIG. 3).

And the results in FIG. 4 showed a dose-response effect of Resv-LA (FIG. 4A) and respectively Resv-C22 (Resv-BE) (FIG. 4B) on the inhibitory activity of MMP9.

Example 3: Effect of Lipophenolic Derivative of Resveratrol on In Vitro Vascular Permeability Assay (FITC-Dextran Endothelial Permeability Assay)

The permeability of HUVEC monolayer seeded on collagen coated semi-permeable inserts was examined using in vitro vascular permeability assay kit, Millipore™ (Paris, France) according to the manufacturer protocol.

Endothelial cells are seeded into the inserts and cultured until complete monolayer formation occurs. After forming confluent monolayer by seeding HUVECs ($4\times10^5$ cells/insert) for 48 hours, medium was replaced with 100 ng/mL TNF-α in medium with and without MMP-9 inhibitors at 10 μM and incubated for 24 hours in $CO_2$ chamber at 37° C. Lipophenolic derivatives of resveratrol were dissolved in DMSO, and SB-3CT (gelatinase inhibitor) was dissolved in DMSO.

At the end of the permeability treatment, 150 μl FITC-dextran in media solution were incubated for 20 minutes at room temperature protected from light. FITC-dextran permeates the treated cell monolayer into the plate well. Permeation was stopped by removing the inserts and 100 μl were withdrawn from the receiving tray and added to 96-well opaque plate for fluorescence measurement. The resulting fluorescence in the plate well is measured and used as an indicator of the extent of monolayer permeability. Filters used are 485 nm and 535 nm for excitation and emission, respectively.

The results are presented in FIG. 5, showing that Resv-LA demonstrated inhibition of TNF-alpha-enhanced permeability of the HUVEC monolayer.

Example 4: Effect of Lipophenolic Derivative of Resveratrol on Cell Viability Assay (Mtt Assay)

The MTT assay is a test used to evaluate the cytotoxicity of compounds.

The cytotoxicity assay was carried out as described by Mosmann (Mosmann 1983). HUVEC cells and THP-1 cell line ($1\times10^4$ cell/well) were seeded in 96-well plate and incubated $CO_2$ incubator chamber at 37° C. for 24 h. Cells were treated with serial dilutions of lipophenolic derivative of resveratrol at a final concentration of 10, 20, 40 and 80 μM, and plate was incubated for 72 hours. Supernatant was discarded and MTT-serum-free medium was added to each plate and incubated for three additional hours. The formed formazan blue crystals were further dissolved by addition of 100 μL of 10% SDS in 0.1 N HCl to each plate for 2 hours. The optical density was measured at 570 nm (reference filter 690 nm) using a TECAN™ plate reader. Lethal Concentration 50% (LC50) was calculated using GraphPad Prism v.5 software.

The results are presented in FIG. 6, showing that Resv-LA and Resv-C22 (Resv-BE) at concentration 10, 20, 40 μM does not have cytotoxic effect on viability.

All these results demonstrate that the lipophenolic compounds of the invention, in particular Resv-LA (FIG. 6A) and Resv-C22 (Resv-BE) (FIG. 6B), have inhibition effect of activity of MMP-9 and are able to decrease the TNF-alpha induced endothelial permeability. Such lipophenolic compounds, as new MMP-9 inhibitors, are capable of protecting the endothelial integrity and decrease the exacerbated vascular permeability, so may be advantageously used to protect the endothelial barrier integrity in infections and other diseases.

Example 5: Effect of Resv-LA (REV-LA) on TNF-α Release by LPS-Activated Microglia Cell Culture BV-2 cells that are derived from raf/myc-immortalised murine neonatal microglia are the most frequently used substitute for primary microglia (Blasi et al., 1990).

BV-2 cells were maintained in 75 cm2 culture flasks in Dulbecco's Modified Eagle's Medium (DMEM, Sigma) supplemented with 10% fetal bovine serum (FBS, Sigma) and 1% Penicillin-Streptomycin solution (Sigma), and cultured at 37° C. in a humidified atmosphere of 5% CO2.

Treatment of the BV-2 Microglial Cell Culture

BV-2 cells were plated on 24-well plates at a density of 105 cells per well. On the following day cells were subjected to different treatments. To study the effect of Resv-LA on TNF-alpha production by LPS activated BV-2 cells, the cells were incubated in medium containing 1 mg/ml LPS (Sigma-Aldrich) for 24 h, with or without Resv-LA (REV-LA) 30 μM.

TNF-Alpha Measurement

Supernatants from untreated and treated cells were centrifuged at 5000 rpm for 5 minutes and assayed for their TNF-α contents using the TNF-α (mouse) AlphaLISA Detection Kit of Perkin-Elmer. TNF-α released was normalized by cell number and expressed as percentage of the maximal released obtained in the LPS-stimulated condition.

Results

REV-LA (30 μM) is efficient for reducing microglial activation and neurotoxic TNF-α secretion by LPS-activated BV2 microglia cells. Twenty-four hours after LPS treatment, TN-α expression was reduced to 66.1±4.2 in REV-LA-treated BV2.

Data are expressed as mean±SEM. Statistical analysis of differences between groups was performed by using unpaired t-test/Mann-Whitney. The level of significance is set at $p<0.05$. *$P<0.05$ and ***$P<0.001$ versus control (Ctr., non LPS-challenged control), #$P<0.05$ ##$P<0.001$ versus LPS-stimulated condition.

The results are presented in the FIG. 7. These data suggest that Resv-LA (REV-LA) inhibits TNF-α release, which is a key factor of inflammatory cascades as disclosed above, so Resv-LA may advantageously be used for preventing or treating central nervous system disorders.

REFERENCES

Blasi, E., Barluzzi, R., Bocchini, V. et al. (1990). Immortalization of murine microglial cells by a v-raf/v-myc carrying retrovirus. J. Neuroimmunol. 27, 229-237

Chang, C. W., C. Y. Wong, Y. T. Wu and M. C. Hsu (2016). "Development of a Solid Dispersion System for Improving the Oral Bioavailability of Resveratrol in Rats." *Eur J Drug Metab Pharmacokinet.*

Cheng, G., X. Zhang, D. Gao, X. Jiang and W. Dong (2009). "Resveratrol inhibits MMP-9 expression by up-regulating PPAR alpha expression in an oxygen glucose deprivation-exposed neuron model." *Neurosci Lett* 451(2): 105-108.

Crauste, C., C. Vigor, P. Brabet, M. Picq, M. Lagarde, C. Hamel, T. Durand and J. Vercauteren (2014). "Synthesis and Evaluation of Polyunsaturated Fatty Acid-Phenol Conjugates as Anti-Carbonyl-Stress Lipophenols." *European Journal Of Organic Chemistry:* 4548-4561.

Delaunay, J. C., C. Castagnino, C. Cheze and J. Vercauteren (2002). "Preparative isolation of polyphenolic compounds from *Vitis vinifera* by centrifugal partition chromatography." *J Chromatogr A* 964 (1-2): 123-128.

Gao, D., T. Huang, X. Jiang, S. Hu, L. Zhang and Z. Fei (2014). "Resveratrol protects primary cortical neuron cultures from transient oxygen-glucose deprivation by inhibiting MMP-9." *Mol Med Rep* 9(6): 2197-2204.

Luplertlop N. et al., 2006. "Dengue-virus-infected dendritic cells trigger vascular leakage through metalloproteinase overproduction (vol 7, pg 1176, 2006). Embo Rep. 2006; 7(12):1290

Marsac D et al. (2011). "Infection of human monocyte-derived dendritic cells by ANDES Hantavirus enhances proinflammatory state, the secretion of active MMP-9 and indirectly enhances endothelial permeability". Virol J. 2011; 8.

Misse D. et al. (2001). "HIV-1 glycoprotein 120 includes the MMP-9 cytopathogenic factor production that is abolished by inhibition of the p38 mitogen-activated protein kinase signaling pathway". Blood. 2001; 98(3):541-7.

Mosmann, T. (1983). "Rapid colorimetric assay for cellular growth and survival: application to proliferation and cytotoxicity assays." *J Immunol Methods* 65(1-2): 55-63.

Walle, T. (2011). "Bioavailability of resveratrol." *Ann N Y Acad Sci* 1215: 9-15.

The invention claimed is:

1. A method for the treatment of encephalitis comprising administering, to a person in need thereof, a compound of formula (IIb):

(IIb)

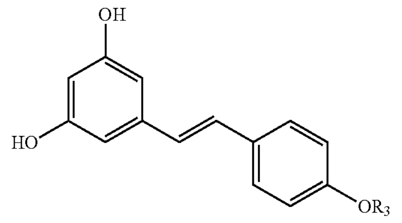

with $R_3$ selected from the group consisting of:

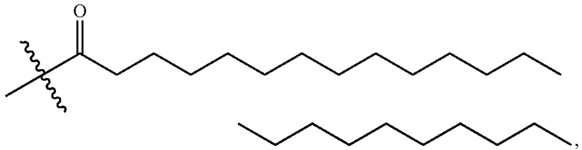

,

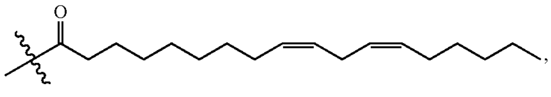

, or

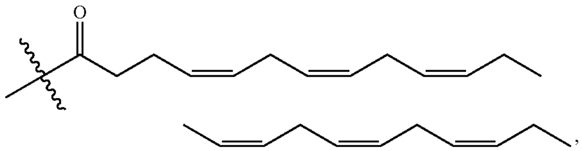

, or its pharmaceutically acceptable salts, racemates, diastereoisomers, enantiomers, or mixtures thereof.

2. The method of claim 1, wherein the compound is administered for 1 to 4 days, and just before and/or during the acute phase response associated with factors inducing the increased vascular, lymphatic or mucosal permeability.

3. The method of claim 1, wherein the compound of formula (IIb) is administered in association with at least one additional active compound selected from the group consisting of antibiotic, antiviral, antifungal, antiparasitic, anti-inflammatory active compound and mixtures thereof.

* * * * *